(12) United States Patent
Miyazawa

(10) Patent No.: US 7,691,097 B2
(45) Date of Patent: Apr. 6, 2010

(54) FOOT SWITCH AND OUTPUT SYSTEM HAVING FOOT SWITCH

(75) Inventor: Taro Miyazawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 744 days.

(21) Appl. No.: 11/212,271

(22) Filed: Aug. 26, 2005

(65) Prior Publication Data
US 2006/0047199 A1   Mar. 2, 2006

(30) Foreign Application Priority Data
Aug. 26, 2004   (JP)   ............................. 2004-246927

(51) Int. Cl.
*A61B 18/00* (2006.01)
(52) U.S. Cl. .......................................... 606/1; 606/34
(58) Field of Classification Search ................ 600/471; 208/86.5; 700/17; 606/1, 32–50
See application file for complete search history.

(56) References Cited

U.S. PATENT DOCUMENTS

| | | | |
|---|---|---|---|
| 5,635,777 A | | 6/1997 | Telymonde et al. |
| 6,054,831 A | * | 4/2000 | Moore et al. ................. 318/581 |
| 6,074,388 A | * | 6/2000 | Tockweiler et al. ............ 606/34 |
| 6,504,117 B2 | * | 1/2003 | Overstreet .................. 200/86.5 |
| 6,539,213 B1 | * | 3/2003 | Richards et al. .......... 455/226.3 |
| 6,893,261 B1 | * | 5/2005 | Feine .......................... 433/101 |
| 7,063,692 B2 | * | 6/2006 | Sakurai et al. ................. 606/1 |
| 7,204,825 B2 | * | 4/2007 | Cimino et al. .............. 604/113 |
| 2002/0081991 A1 | | 6/2002 | Eichin et al. |
| 2002/0156466 A1 | * | 10/2002 | Sakurai et al. ................. 606/1 |

FOREIGN PATENT DOCUMENTS

| | | |
|---|---|---|
| DE | 197 30 456 A1 | 1/1999 |
| EP | 0 891 745 B1 | 1/1999 |
| JP | 5-23347 | 2/1993 |
| WO | WO 02/49509 A2 | 6/2002 |
| WO | WO 2004/008413 A2 | 1/2004 |

\* cited by examiner

*Primary Examiner*—Michael Peffley
*Assistant Examiner*—Ronald Hupczey, Jr.
(74) *Attorney, Agent, or Firm*—Scully, Scott, Murphy & Presser, P.C.

(57) ABSTRACT

The foot switch includes a pedal, an output command signal generating section generating, when the pedal is operated, an output command signal commanding an apparatus main body having a function of producing active output to produce active output, a communication section performing communication with the apparatus main body, a transmit power adjusting section adjusting transmit power of the output command signal in the communication section, and a storage battery supplying electric power to the output command signal generating section, the communication section and the transmit power adjusting section. The transmit power adjusting section adjusts the transmit power on the basis of a signal indicative of receiving-condition of the output command signal in the apparatus main body, the signal transmitted from the apparatus main body and received by the communication section.

12 Claims, 15 Drawing Sheets

FOOT SWITCH AND OUTPUT SYSTEM HAVING FOOT SWITCH

CROSS-REFERENCE TO RELATED APPLICATION

This application is related to Japanese Patent Application No. 2004-246927 filed on Aug. 26, 2004, the contents of which are hereby incorporated by reference.

BACKGROUND OF THE INVENTION

1. Technical Field

The present invention relates to a foot switch which transmits a signal for commanding generation of active output to an apparatus main body having a function of generating active output, and relates to an output system including such a foot switch and an apparatus main body.

2. Related Art

One example of such an output system is an ultrasonic surgical system disclosed in Japanese Unexamined Patent Application Publication No. 05-023347. An apparatus main body of this ultrasonic surgical system includes a main unit for generating drive signals (high frequency voltage signals). A handpiece having a probe at a tip thereof and gripped by the operator is electrically connected to the main unit through a cable. The handpiece includes therein an ultrasonic transducer which converts the drive signals into mechanical vibration (ultrasonic band signals). The ultrasonic vibration generated by the ultrasonic transducer is transmitted to the probe while being amplified. A water supply/suction path is provided in the handpiece and the probe. The system is so arranged that when the water supply/suction path is connected to a water supply/suction device, water supply/suction treatment can be effected through an opening formed at an end face of the probe and its vicinity.

More specifically, treatment can be performed by destroying and emulsifying tissues such as of liver parenchyma while performing perfusion through the opening formed in the ultrasonically vibrating probe, and by sucking/removing the debris together with the superfusate through the supply/suction path. An electric knife system may be used together with such an ultrasonic surgical system. Hemostatic treatment or the like can be effected by connecting the electric knife to the handpiece to make a high frequency output through the handpiece of the electric knife.

Since the treatment device including the handpiece or an electric knife is gripped by the operator during surgery, it is appropriate that on/off operation of the treatment device is performed through a foot switch except for a case where a pinpoint operation is particularly required (for example, when hemostatic treatment is performed by the electric knife). That is because, since depressing a switch for a long time with fingers to keep a treatment device in an on-state is a great burden to the operator, employing a foot switch which enables the operator to keep depressing the switch by the operator's weight is desirable from an ergonomical point of view.

It is to be noted that in order to enable selection from among different output types, for example, selection between water supply operation and suction operation, a plurality of pedals are generally disposed in a foot switch. A foot switch is required to have an excellent user-interface design so that the operator can readily distinguish the plurality of pedals.

A foot switch is typically electrically connected to an apparatus main body through a cable to transmit the operational statuses of the foot switch pedals to the apparatus main body through the cable. When using a plurality of different output systems in surgical operation (e.g., when using an ultrasonic surgical system and an electric knife system), a plurality of foot switches are used. The plurality of foot switches are placed close to the operator's feet, and used while there locations are permutated depending on the progress of the surgical operation. In such a case, however, the cables of the plurality of the foot switches sometimes tangle with each other, which significantly lowers the operator's convenience since appropriate locations of the foot switches cannot be ensured. Particularly, in advanced manipulation in which the operator often keeps moving around the operating table during a surgical operation, since the locations of the foot switches are required to be changed following the operator's movement even in a particular case, the chance of the occurrences of the cable tangling increases that much.

In order to prevent surgical operation from stopping due to such tangling of cables, it is known as described in U.S. Pat. No. 6,074,388, for example, to transfer the operational statuses of the pedals of a foot switch to an apparatus main body by means of radio communication. The foot switch in the surgical system described in the '388 patent incorporates a battery as a power source, and is arranged such that a warning is displayed in a display device at an appropriate time, so as to prevent interruption of a surgical operation by the low output voltage of the battery resulting from electrical discharge of the battery. The foot switch is also provided with an auxiliary battery.

Here, in the case of transferring the operational statuses of a foot switch pedal to an apparatus main body by radio communication, the required transmit power of radio signals depends on the use environment of use of the surgical system. For example, if noise caused by the use of an electric knife, and affecting the radio signals is at a high level, or the foot switch is distant from the apparatus main body, or there is an electromagnetic obstacle, the transmit power of radio signals should be made large. Contrarily, if the noise is at a low level, or the foot switch is close to the apparatus main body, or there is not any electromagnetic obstacle, it is satisfactory possible to transfer the operational statuses of the foot switch pedal to the apparatus main body even if the transmit power of the radio signals is relatively low.

However, in such a surgical system in which the operational status of the foot switch pedal is transferred to the apparatus main body by radio communication, transmit power of radio signals has to be set at a comparatively high level, so that the communication between the foot switch and the apparatus main body can be maintained even when there occurs a change in the use environment of the surgical system. Accordingly, the period during which the foot switch can be used, i.e. the period during which power can be supplied by a battery, is reduced. In the surgical system described in the '388 patent, the period during which the foot switch is usable can be extended by incorporating an auxiliary battery in the foot switch. However, the incorporation of such an auxiliary battery causes the size and weight of the foot switch to increase, and thus a problem of poor portability is also an issue.

SUMMARY OF THE INVENTION

The present invention has been made to eliminate the problem described above with an object to provide a compact foot switch that can be used for long hours, and to provide an output system having such a foot switch.

In order to achieve the above object, the present invention provides an output system including a foot switch and an apparatus main body having a function of producing active output, the foot switch including:
a pedal;
an output command signal generating section generating an output command signal when the pedal is operated;
a foot switch communication section performing communication with the apparatus main body;
a transmit power adjusting section adjusting transmit power of the output command signal in the foot switch communication section; and
a storage battery supplying electric power to the output command signal generating section, the foot switch communication section, and the transmit power adjusting section, the apparatus main body including:
a main body communication section performing communication with the foot switch;
an active output producing section producing active output in accordance with the output command signal transmitted from the foot switch and received by the main body communication section; and
a receiving-condition detecting section detecting receiving condition of the output command signal in the main body communication section and generating a signal indicative of the detected receiving condition, wherein the transmit power adjusting section adjusts the transmit power on the basis of the signal indicative of the detected receiving condition, the signal being detected by the receiving-condition detecting section, transmitted from the main body communication section and received by the foot switch communication section.

In the output system described above, the transmit power on the foot switch side is automatically adjusted to a proper power level. Accordingly, with this output system, it is possible to reduce power consumption of the foot switch while ensuring the radio communication between the foot switch and the apparatus main body.

In order to achieve the above object, the present invention also provides an output system including a foot switch and an apparatus main body having a function of producing active output, the foot switch including:
a pedal;
an output command signal generating section generating an output command signal when the pedal is operated;
a foot switch communication section transmitting the output command signal to the apparatus main body; and
a storage battery supplying electric power to the output command signal generating section, and the foot switch communication section, the apparatus main body including:
a main body communication section receiving the output command signal transmitted from the foot switch; and
an output producing section producing active output in accordance with the output command signal received by the main body communication section;

wherein the output command signal generating section generates a train of regularly spaced pulses as the output command signal while the pedal is operated.

In the output system described above, the radio communication between the apparatus main body and the foot switch is carried out by using pulse-like signals which are transmitted at regular intervals. Accordingly, the power consumption of the foot switch of this output system is significantly small compared to conventional systems in which the output command signal is transmitted in a continuous manner.

Other configurations and advantages of the present invention will be apparent from the descriptions on the embodiments and the accompanying drawings provided hereunder.

DETAILED DESCRIPTION OF THE PREFERRED EMBODIMENTS

Figure 1:
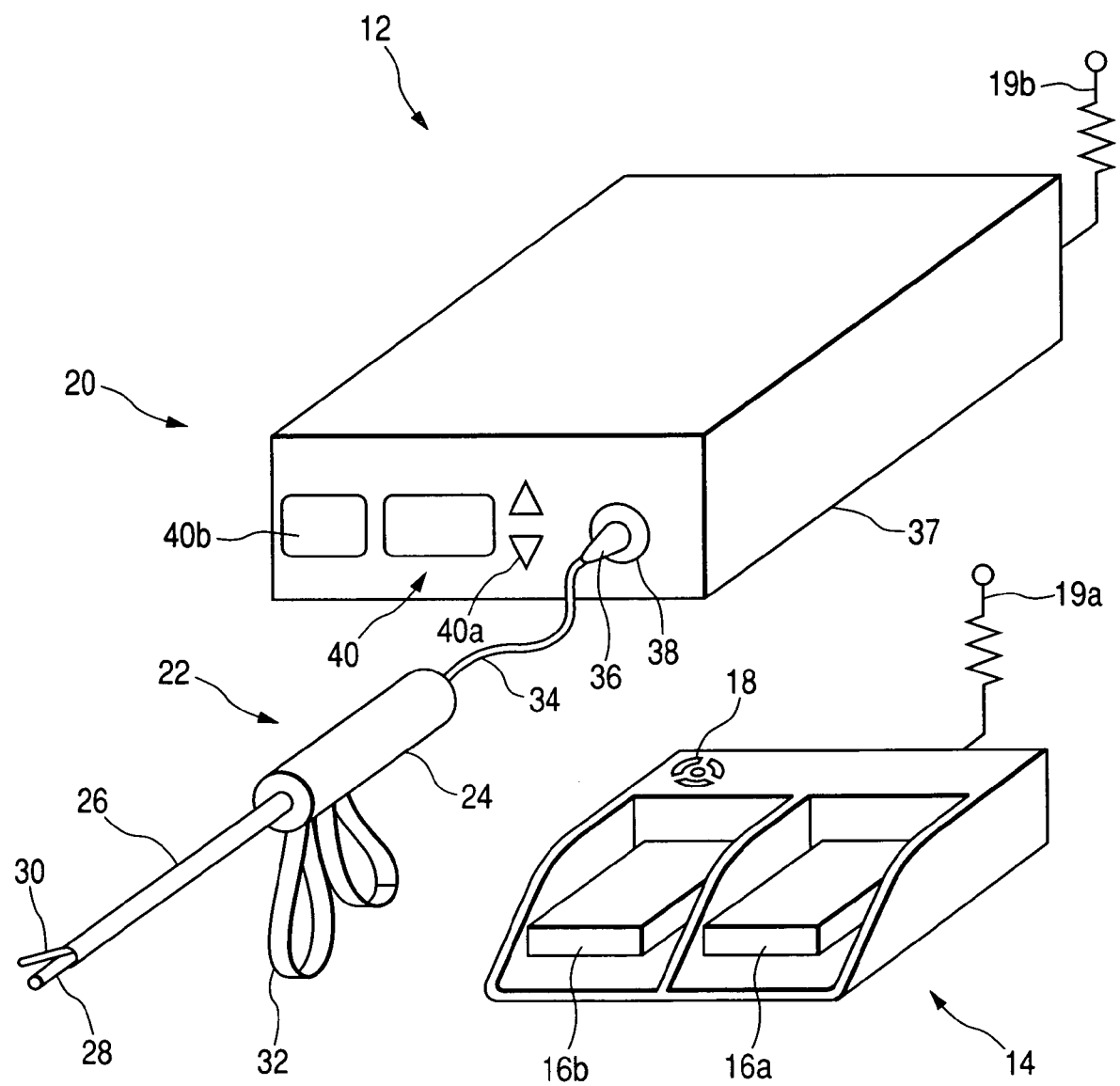
FIG. 1 is a perspective view illustrating the appearances of an apparatus main body and a foot switch of an ultrasonic surgical system of a first embodiment according to the present invention.

Several ultrasonic surgical systems using a foot switch of the invention are described below as output systems. In the below described embodiments, identical reference characters are used for identical or corresponding parts.

Figure 2:
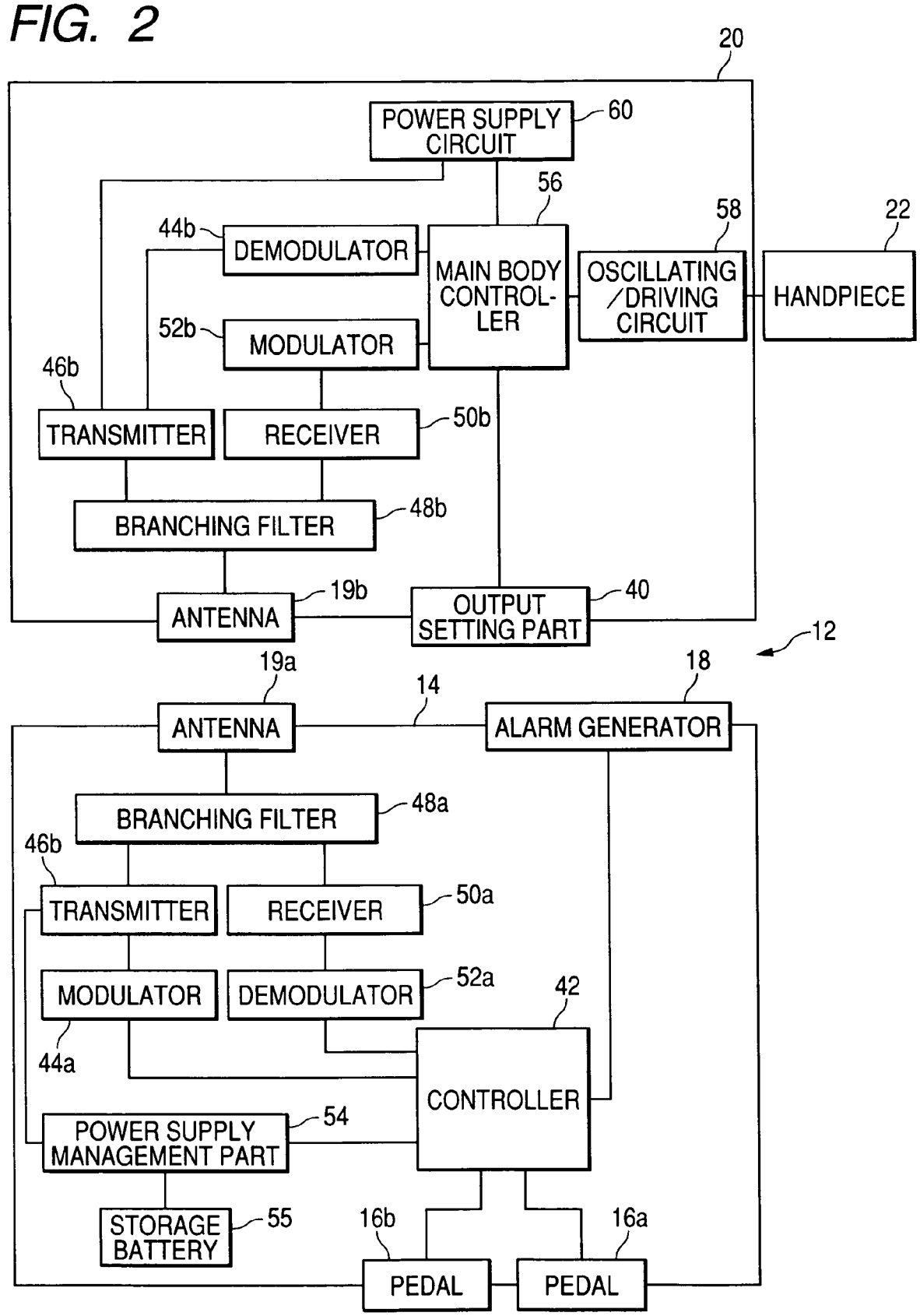
FIG. 2 is a block diagram illustrating circuitries of the apparatus main body and the foot switch of the ultrasonic surgical system of the first embodiment according to the present invention.

With reference to FIGS. 1 to 9, the first embodiment according to the present invention is described. An ultrasonic surgical system 12 includes a foot switch 14 and an apparatus main body 20 having respective appearances as shown in FIG. 1 and having respective circuitries as shown in FIG. 2.

As shown in FIG. 1, the foot switch 14 includes first and second pedals 16a, 1 b which are depressed by the operator's foot, a buzzer 18 serving as an alarm generator which generates warning in case of malfunction, and an antenna 19a for performing radio communication.

As shown in FIG. 1, the apparatus main body 20 includes a main unit 37, and a handpiece 22 having a gripper 24 gripped by the operator, which is detachably connected to the main unit 37 through a cable 34. A sheath 26 having a probe 28 being inserted therethrough is connected to a front end of the gripper 24. A tip of the probe 28 is projected from the sheath 26. A rear end of the probe 28 is connected to an ultrasonic transducer, not shown, which is disposed inside the gripper 24. A jaw 30 is disposed at a tip of the sheath 26, for holding an object to be treated cooperating with the tip of the probe 28. The jaw 30 is configured to be in contact with or apart from the probe 28, interlocking with the opening/closing operation of a handle 32 disposed at the gripper 24.

The cable 34, with its one end being connected to a connector 36, serves to supply a driving signal (AC voltage signal) from the main unit 37 to the ultrasonic transducer, not shown, disposed in the gripper 24. The connector 36 is connected to a corresponding connector 38 at a front face of the main unit 37. An output setting part 40 is disposed at the front face of the main unit 37 so as to control the intensity of ultrasonic output of the handpiece 22. The output setting part 40 comprises an output setting switch 40a for setting the ultrasonic output intensity, and a display 40b for displaying the output intensity that has been set. An antenna 19b is disposed at a rear of the main unit 37, for performing radio communication with the foot switch 14.

In the following description, the signal transmitted from the foot switch 14 to the apparatus main body 20 is referred to as a foot switch signal, and the signal transmitted from the main unit 37 of the apparatus main body 20 to the foot switch 14 is referred to as a main unit signal.

The foot switch signal includes a foot switch identification ID, a pedal open/close signal, and a main unit transmit power-UP command signal. The foot switch identification ID and the pedal open/close signal are collectively referred to as signal information.

The foot switch identification ID is an ID unique to the individual foot switch 14, which is used for distinguishing the foot switch 14 from other foot switches of the same kind. The pedal open/close signal is a signal for notifying the apparatus main body 20 as to whether the first pedal 16a or the second pedal 16b is in a closed state (the state of being depressed) or in an open state (the state of being released). In case the pedal open/close signal is indicative of the closed state of the first pedal 16a or the second pedal 16b, the apparatus main body 20 outputs ultrasonic vibration generated by the ultrasonic transducer, and in case the signal is indicative of the closed state, the output of the ultrasonic vibration is stopped.

When the main unit signal transmitted from the apparatus main body 20 side is difficult to receive, the foot switch 14 transmits the main unit transmit power-UP command signal which is a signal commanding the main unit 37 of the apparatus main body 20 to increase its transmit power (hereinafter referred to as the MU-UP signal (Main Unit output Upward signal)) to the apparatus main body 20. Upon receipt of the MU-UP signal the apparatus main body 20 increases the transmit power of the main unit signal.

The main unit signal is a signal which is transmitted from the foot switch 14 to the apparatus main body 20 in response to the foot switch signal, and includes a main body identification ID, a signal commanding the foot switch 14 to increase or reduce it transmit power, and an ultrasonic output stop signal.

The main body identification ID is an ID unique to the individual apparatus main body 20, and is for distinguishing the apparatus main body 20 from other apparatus main bodies.

When the receive power of the received foot switch signal is lower than a predetermined level (e.g., −50 dB), which is settable at any value, the apparatus main body 20 transmits a signal commanding the foot switch 14 to increase its transmit power (hereinafter referred to as the FSW-UP signal (Foot Switch output Upward signal)) to the foot switch 14. On the other hand, when the receive power of the received foot switch signal is equal to or higher than the predetermined level, the apparatus main body 20 transmits a signal commanding the foot switch 14 to reduce its transmit power (hereinafter referred to as the FSW-DOWN signal (Foot Switch output Downward signal)) to the foot switch 14. Upon receipt of the FSW-UP command signal, the foot switch 14 increase the transmit power of the foot switch signal. Contrarily, upon receipt of the FSW-DOWN command signal, the foot switch 14 reduce the transmit power of the foot switch signal.

An ultrasonic output stop signal is a signal which is transmitted to the foot switch 14 from the apparatus main body 20, when the output of ultrasonic vibration is stopped in response to the pedal open/close signal, to notify the foot switch 14 of this.

The internal configurations of the foot switch 14 and the apparatus main body 20 are described below with reference to FIG. 2.

As shown in FIG. 2, the foot switch 14 includes therein a storage battery 55, a power supply management part 54, a controller 42, a modulator 44a, a transmitter 46a, a branching filter 48a, a receiver 50a, and demodulator 52a.

The pedal open/close signal indicative of open/closed state of the first pedal 16a or the second pedal 16b is inputted to the controller 42. The controller 42 produces the foot switch signal by adding the foot switch identification ID which is unique to the individual foot switch 14 to the pedal open/close signal.

For the communication between the apparatus main body 20 and the foot switch 14, the main unit signal transmitted from the apparatus main body 20 is received by the antenna 19a, and then sent to the receiver 50a by way of the branching filter 48a. Further, this main unit signal is demodulated by the demodulator 52a and inputted to the controller 42. When it is difficult to correctly recognize the main unit signal in the controller 42, the MU-UP signal is produced by the controller 42 which serves also as a transmit power adjusting section to increase the transmit power of the main unit signal. As the basis for determining the difficulty of recognition, an error rate of the received main unit signal is calculated, for example. The controller 42 produces the MU-UP signal, for example, when the error rate of the received main unit signal is equal to or more than a predetermined threshold value (e.g., 0.03%).

In case the MU-UP signal has been produced, the controller 42 adds this MU-UP signal to the foot switch signal. The foot switch signal is modulated by the modulator 44a so as to have a frequency suitable for mutual communication, and transmitted to the apparatus main body 20 by the transmitter 46a through the branching filter 48a and the antenna 19a.

When the main unit signal is inputted, the controller 42 also controls, in accordance with the FSW-UP signal or FSW-DOWN signal contained in the main unit signal, the power supply management part 54 which serves as a transmit power adjusting section. Specifically, so when the FSW-UP signal is inputted, the controller 42 controls the power supply management part 54 such that the power supplied from the storage battery 55 to the transmitter 46a is increased by one level to thereby increase the transmit power of the foot switch signal by one level, and that, when the FSW-DOWN signal is inputted, the power supplied from the storage battery 55 to the transmitter 46a is reduced by one level to thereby reduce the transmit power of the foot switch signal by one level.

While the receive power of the foot switch signal in the apparatus main body 20 is lower than a reference level that can be set at an optional level (referred to as the reference level OL hereinafter), the transmit power of the foot switch signal in the foot switch 14 is increased stepwise by the control of the controller 42 as described above. However, when the transmit power of the foot switch signal exceeds a specified upper limit value (referred to as the value UV hereinafter), the controller 42 determines malfunction as having occurred and stops transmission of the foot switch signal. In this case, an alarm generator 18 raises an alarm. In the present embodiment, the buzzer is sounded.

On the other hand, while the receive power of the foot switch signal in the apparatus main body 20 is equal to or more than the reference level OL, the transmit power of the foot switch signal in the foot switch 14 is reduced stepwise. However, the controller 42 controls the power supply management part 54 so that the receive power of the foot switch signal does not go beyond a specified lower limit value referred to as the value LV hereinafter). The object of this operation is to avoid communication interruption due to noise or the like while conforming to radio by keeping the transmit power at a certain level and providing upper and lower limits.

Thus, the modulator 44a, transmitter 46a, branching filter 48a, antenna 19a, receiver 50a, and demodulator 52a form a foot switch communication section which transmits the foot switch signal and receives the main unit signal.

As shown in FIG. 2, the apparatus main body 20 comprises therein a power circuit 60, a main body controller 56, an oscillating/driving circuit 58, a modulator 44b, a transmitter 46b, a demodulator 52b, a receiver 50b and a branching filter 48b.

The foot switch signal which has been transmitted from the foot switch 14 and received by the antenna 19b, is separated from the main unit signal by the branching filter 48b and inputted to the receiver 50b. The foot switch signal is then demodulated by the demodulator 52b and inputted to the main body controller 56.

Foot switch identification IDs, which are assumed to be used with the apparatus main body 20, are stored in a memory, not shown, in the main body controller 56. The main body controller 56 performs the following operations when detecting an identification ID included in received foot switch signal used for identification with an identification ID stored in the memory.

When the pedal open/close signal included in the foot switch signal indicates the first pedal 16a or the second pedal 16b to be in an open state, the main body controller 56 supplies a drive signal (AC voltage signal) to the ultrasonic transducer disposed in the gripper 24 of the handpiece 22, by oscillating the oscillating/driving circuit 58. The ultrasonic transducer then converts the drive signal into mechanical vibration to thereby generate ultrasonic vibration. The operator may set an output intensity of the ultrasonic vibration by operating the output setting part 40.

In the present embodiment, when the second pedal 16b is being depressed, the ultrasonic transducer vibrates with an intensity set at the output setting part 40, and when the first pedal 16a is being depressed, the ultrasonic transducer constantly vibrates with a maximum output intensity irrespective of the intensity set at the output setting part 40.

Thus, the main body controller 56, oscillating/driving circuit 58 and the handpiece 22 form the output producing section for the apparatus main body 20.

If the pedal open/close signal indicates that both of the first and second pedals 16a, 16b are in the open state, the main body controller 56 has to cause the oscillating/driving circuit 58 to stop the oscillation to thereby stop the ultrasonic vibration of the handpiece 22. In this case, the main body controller 56 forms a main unit signal by producing an ultrasonic output stop signal and by attaching thereto the identification ID included in the received foot switch signal.

The main body controller 56 produces the FSW-UP signal when the receive power of the foot switch signal is lower than the reference 36 level OL, and when the receive power is equal to or higher the reference level OL, produces the FSW-DOWN signal. Thus, in the present embodiment, the main body controller 56 constitutes a receiving-condition detecting section for detecting a receiving condition based on the receive power of the foot switch signal.

The main body controller 56 forms the main unit signal by adding the identification ID included in the received foot switch signal to the FSW-UP signal or FSW-DOWN signal.

The main unit signal is modulated so as to have a suitable frequency, and transmitted to the foot switch 14 by the transmitter 46b through the branching filter 48b and the antenna 19b. The transmit power of the main unit signal is controlled depending on the presence of the MU-UP command signal in the received foot switch signal. Particularly, if the MU-UP command signal is present in the received foot switch signal, the main body controller 56 controls the power supply circuit 60, such that the power supplied to the transmitter 46b is increased, and thereby the transmit power of the main unit signal is increased.

Thus, a main body communication section which receives the foot switch signal and transmits the main unit signal is constituted by the modulator 44b, transmitter 46b, branching filter 48b, antenna 19b, receiver 50b and the demodulator 52b. The main body communication section and the foot switch communication section of the foot switch 14 perform signal transmission therebetween according to a common protocol. For this signal transmission, an antenna power of 10 mW or 26 more in 2.4 GHz ISM band assigned to medical devices as specified low power radio stations can used within a scope that does not affect other devices.

Figure 3:
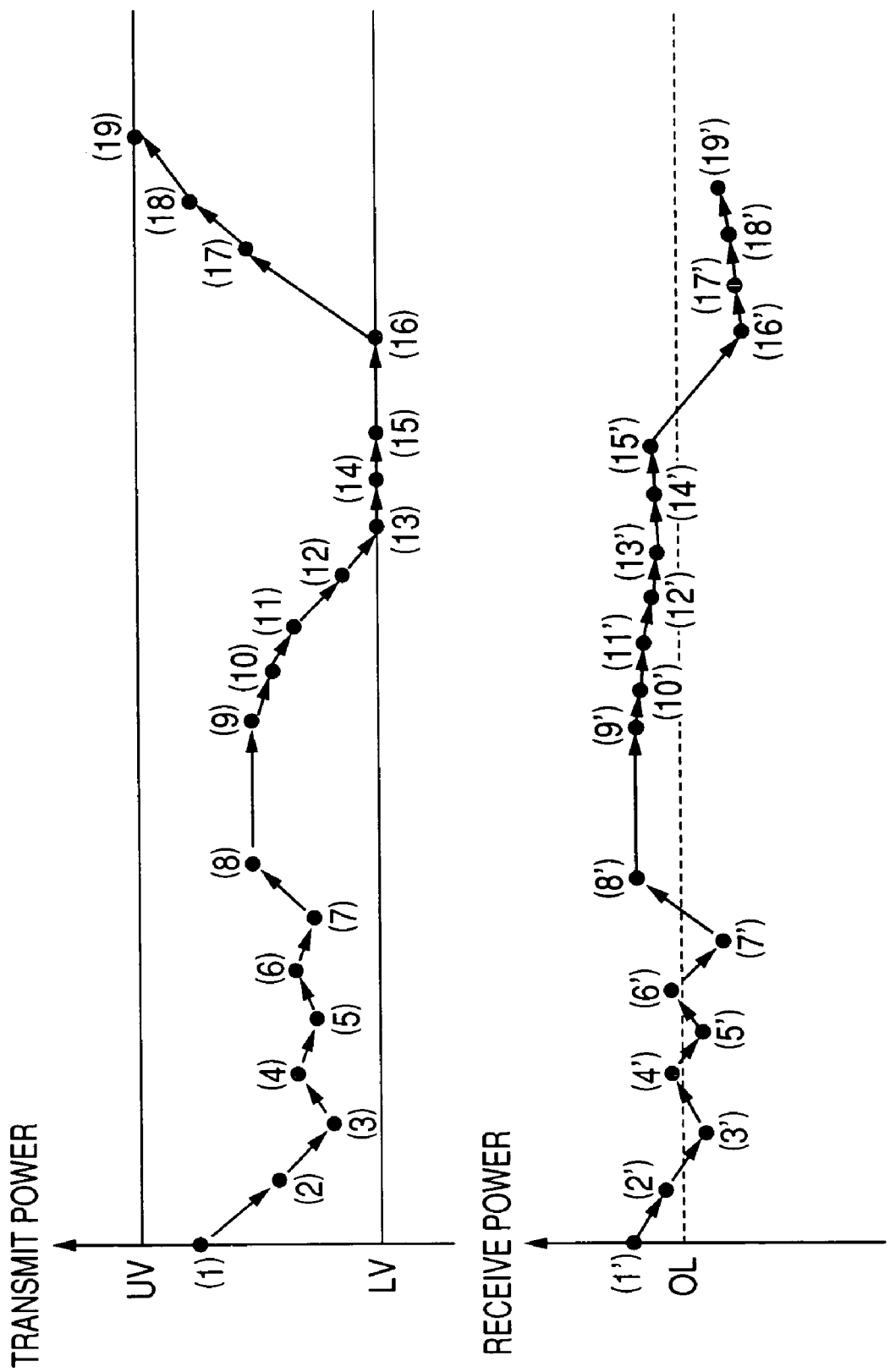
FIG. 3 is a diagram showing temporal variations of the transmit powers of foot switch signals transmitted from the foot switch to the apparatus main body, and of the receive power of the foot switch signals received by the apparatus main body, in the ultrasonic surgical system of the first embodiment according to the present invention.

Referring to FIG. 3, an example is described hereunder of temporal variations of the transmit power and receive power of the foot switch signals in the ultrasonic surgical system 12 having the configuration described above.

When the foot switch 14 transmits the foot switch signal with a transmit power of level (1) and the apparatus main body 20 receives the foot switch signal with a receive power of level (1'), if the level (1') is equal to or higher than the reference level OL, the FSW-DOWN signal is transmitted to the foot switch 14 from the apparatus main body 20. As a result, the transmit power is reduced from level (1) to level (2).

When the foot switch signal is transmitted with the transmit power of level (2) and received with a receive power of level (2'), if the level (2') is still equal to or higher the reference level OL, the transmit power is further reduced from level (2) to level (3).

Further, when the foot switch signal is transmitted with the transmit power of level (3) and received with a receive power of level (3'), if the level (3') is lower than the reference level OL, the FSW-UP command signal is transmitted from the apparatus main body 20 to the foot switch 14. As a result, the transmit power is increased from level (3) to level (4).

Furthermore, when the foot switch signal is transmitted with the transmit power of level (4) and received with a receive power of level (4'), if the level (4') is equal to or higher than the reference level OL, the transmit power is reduced from level (4) to level (5).

Likewise, transmit power is sequentially set at level (6), level (7), level (8), etc., so that receive power may fluctuate in the vicinity of the reference level OL.

Likewise, thereafter, when the foot switch signals is transmitted with a transmit power of level (9) and received with a receive power of level (9'), if the level (9') is equal to or higher than the reference level OL, the transmit power is reduced from level (9) to level (10).

Assume that, in spite of a sequential reduction of transmit power from level (10), level (11), level (12), etc., a level of receive power hardly reduces (level (10'), level (11'), level (12'), etc. in FIG. 3). In this case, as shown in FIG. 3, if the transmit power is reduced down to level (13) that corresponds to the value LV, no further reduction in transmit power occurs. Thus, when the transmit power is reduced to a level (13) corresponding to the value LV, even if a receive power is at a level exceeding the reference level OL (i.e., level (13'), level (14') or level (15')), transmit power is maintained at a level corresponding to the value LV (level (14), level (15), level (16) in FIG. 3).

However, as shown in FIG. 3, in case the receive power of the foot switch signal is suddenly lowered to a level (16') which is lower than the reference level OL, the transmit power is increased from level (16) to level (17) to follow this lowering of the receive power.

Assume that, in such a case, in spite of a sequential increase of the transmit power to level (17), level (18), level (19), the level of receive power hardly increases (level (17'), level (18'), level (19') in FIG. 3). In this case, if the transmit power reaches a level (20) that corresponds to the value UV, transmission of the foot switch signal is stopped and the buzzer is sounded to inform the operator of the occurrence of malfunction, because there is the possibility of the transmit power exceeding the regulation limit.

With reference to the flow diagrams of FIGS. 4 to 8, the operational process of the ultrasonic surgical system of the present embodiment is described below.

Figure 4:
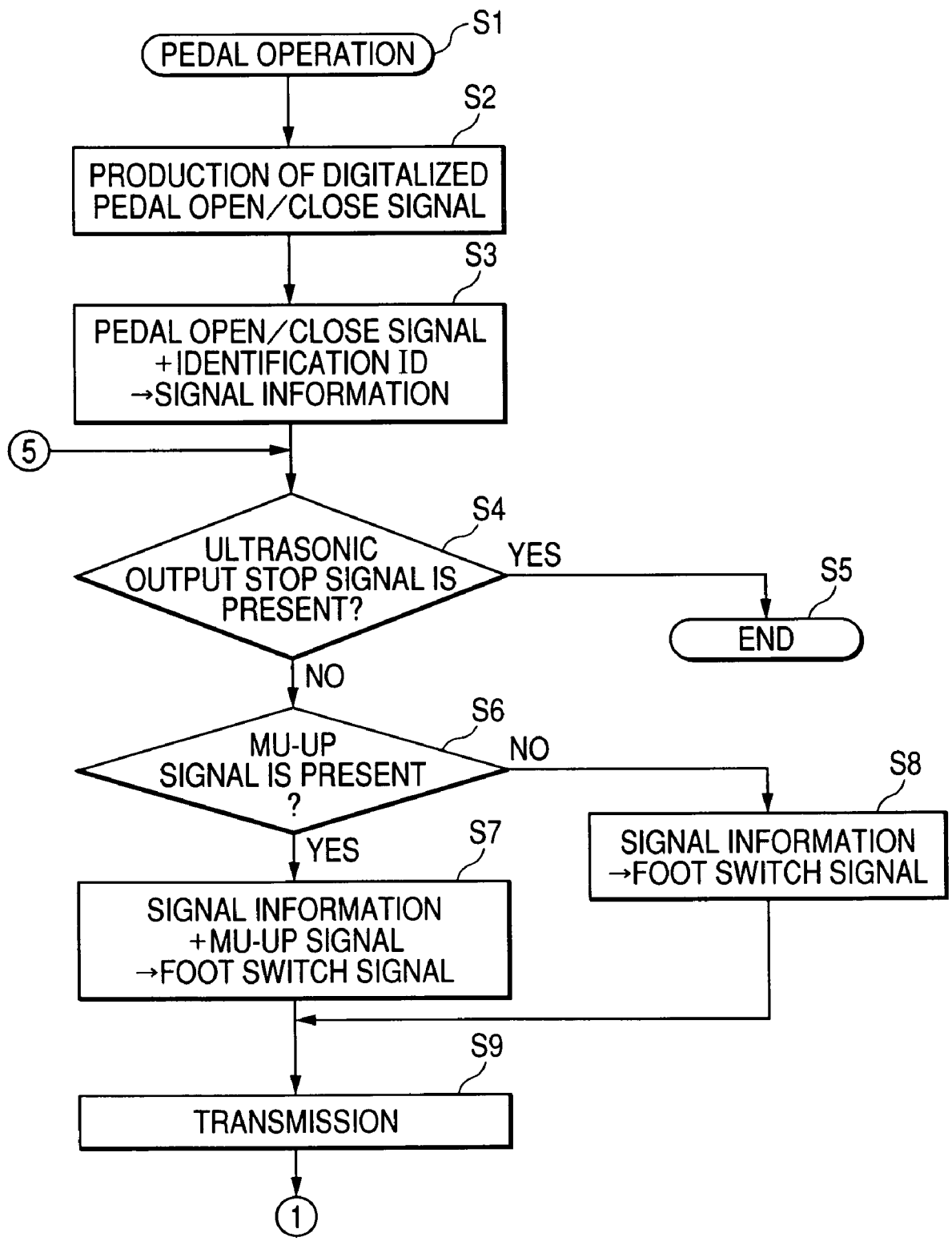
FIGS. 4 to 8 are flow diagrams illustrating the operations of the ultrasonic surgical system of the first embodiment according to the present invention.

When the first pedal 16a or the second pedal 16b of the foot switch 14 is operated at step S1 shown in FIG. 4, the controller 42 produces the digitalized pedal open/close signal, at step S2, indicative of either an open state (hereinafter referred to as a pedal-open state) or a closed state (hereinafter referred to as a pedal-closed state) of the pedal 16a or 16b. At step S3, the controller 42 produces signal information by adding an identification ID unique to the individual foot switch 14 to the pedal open/close signal.

Here, as will be described later, if the pedal open/close signal transmitted from the foot switch 14 to the apparatus main body 20 indicates a pedal-open state, a responsive ultrasonic output stop signal is returned from the apparatus main body 20 to the foot switch 14. Thus, checking is performed, at step S4, as whether or not an ultrasonic output stop signal has been received. If it is determined that the ultrasonic output stop signal has been received, at step S4, the operational process is terminated (step S5). Contrarily, if it is determined that the ultrasonic output stop signal has not been received, the operational process moves to step S6.

At step S6, checking is performed as to whether or not the MU-UP signal has been produced. As explained above, the MU-UP signal is for commanding the apparatus main body to increase the transmit power if it is difficult to recognize the main unit signal received from the apparatus main body 20. If it is determined, at step S6, that the MU-UP signal has been produced, the foot switch signal is produced at step S7 by adding the MU-JP signal to the signal information, and thereafter, the operational process moves to step S9.

On the other hand, if it is determined, at step S6, that the MU-UP signal has not been produced, instead of the MU-UP signal, a null (zero signal) is added to the signal information to produce the foot switch signal at step S8, and then the operational process proceeds to step S9. At step S9, the foot switch signal is transmitted from the foot switch 14 to the apparatus main body 20.

Figure 5:
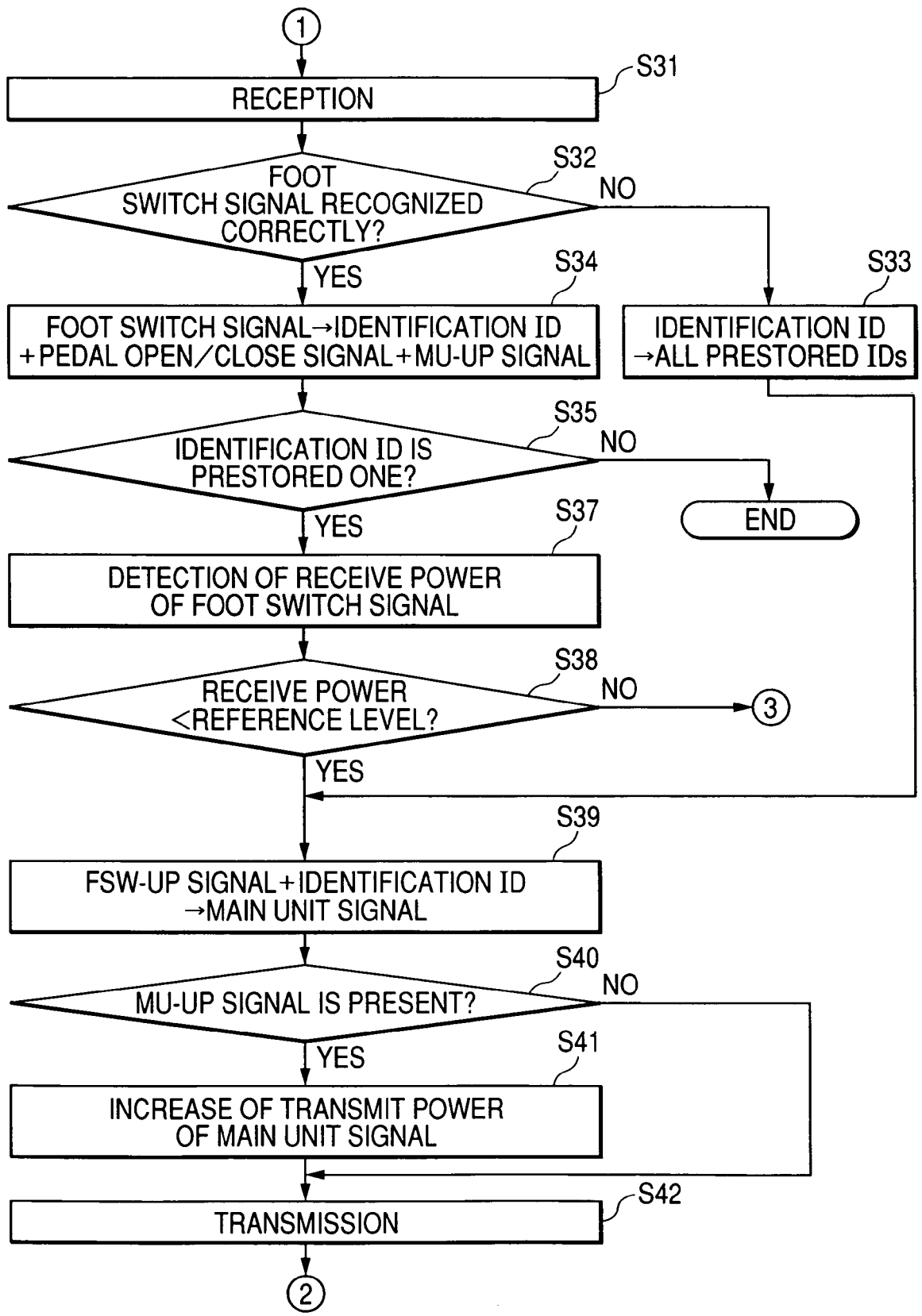
Figure 6:
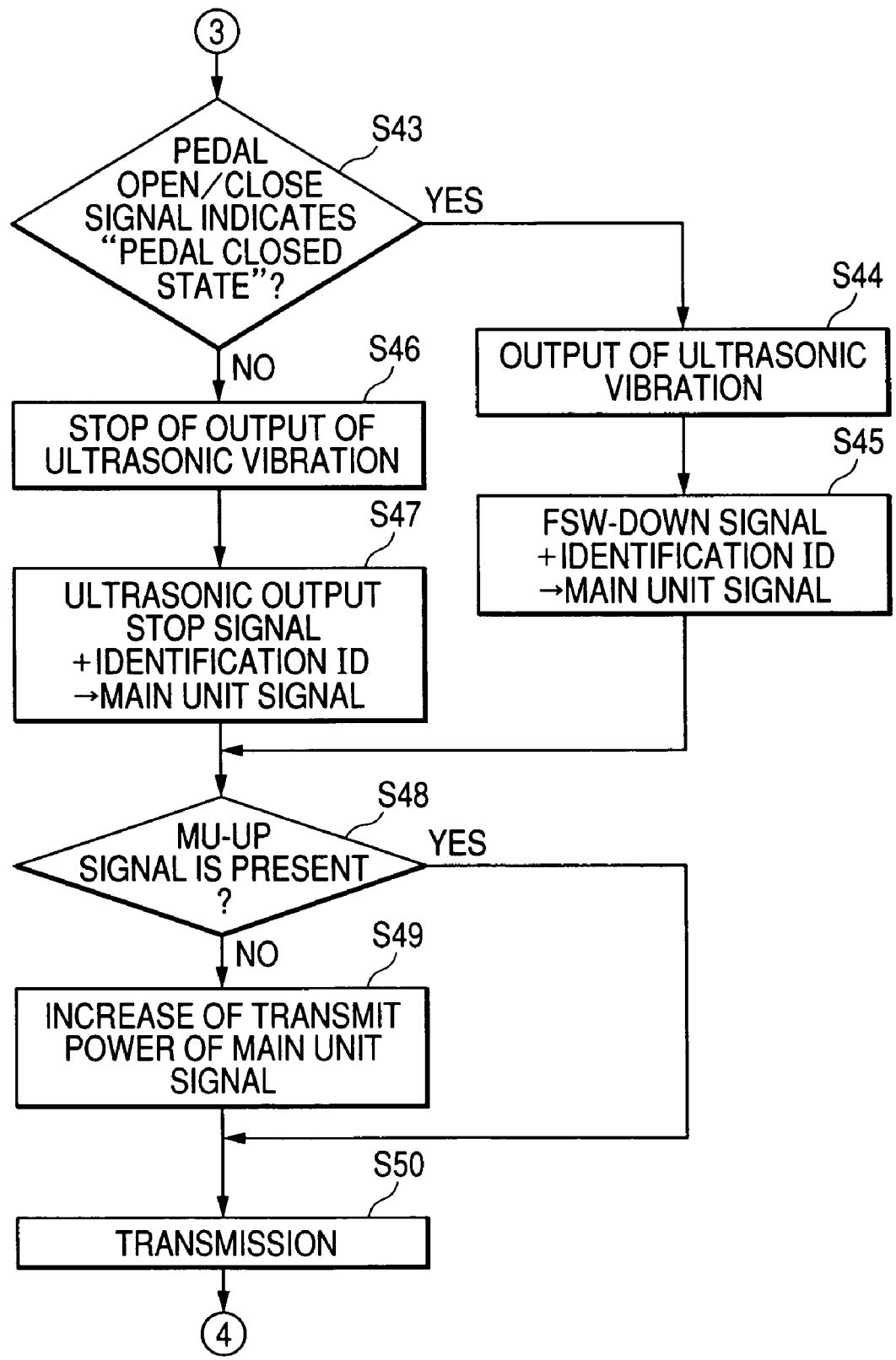

On the other hand, at the side of the apparatus main body 20, checking is performed as to whether or not the foot switch signal which has been received at step S31 shown in FIG. 5 and demodulated by the demodulator 52b can be correctly recognized by the main body controller 56 at step S32. If the foot switch signal cannot be correctly recognized at step S32, it means that it is not possible to extract, from the foot switch signal, the identification ID of the foot switch 14 performing the mutual communication. In this case, the operational process proceeds to step S33. At step S33, all of the foot switch identification IDs registered in the apparatus main body 20 as connection target candidates are selected in place of the identification ID which should have been extracted from the foot switch signal, and then the operational process proceeds to step S39.

Contrarily, if the foot switch signal is determined as having been correctly recognized, the operational process proceeds to step S34. At step S34, the main body controller 56 extracts the identification ID, pedal open/close signal and MU-UP signal from the foot switch signal. Incidentally, if the foot switch 14 has correctly recognized the main unit signal at step S6, and no MU-UP command has been produced, it is determined that the MU-UP signal is null and not included as any command signal in the foot switch signal.

At the next step S35, the main body controller 56 checks whether or not the extracted identification ID matchs one of the identification IDs registered in the apparatus main body 20. If the extracted identification ID is determined as not being identical with any of the registered identification IDs, the main body controller 56 determines that the received foot switch signal is the one transmitted from an unexpected foot switch 14 (or a foot switch 14 out of scope), and terminates the operational process for the signal transmitted from this unexpected foot switch 14 (step S36).

On the other hand, if the extracted identification ID is determined, at step S35, as being identical with one of the registered identification IDs by the apparatus main body 20, the main body controller 56 determines that mutual authentication between the apparatus main body 20 and the foot switch 14 has been performed, and calculates, at the next step S37, the degree of the receive power of the foot switch signal. Subsequently, the detected receive power is compared, at step S38, with the reference level OL. If the receive power is determined, at step S38, as being lower than the reference level OL, the operational process moves to step S39.

When the foot switch signal is determined, at step S32, as not having been correctly recognized as described above, and when the receive power of the foot switch signal is determined, at step S38, as being lower than the reference level OL, the operational process proceeds to step S39. At step S39, the main body controller 56 produces the main unit signal by producing the FSW-UP signal and by adding the identification ID contained in the received foot switch signal to this FSW-UP signal. However, in case that the foot switch signal has not been correctly recognized, and thus any identification ID has not been extracted, the main body controller 56 produces the main unit signal by adding all the registered foot switch identification IDs to this FSW-UP signal.

At the next step S40, the received foot switch signal is checked as to whether or not any MU-UP signal is present therein. If it is determined that the MU-UP signal is not present, that is, determined that the signal corresponding to the MU-UP signal is null the operational process proceeds to step S42.

Contrarily, if it is determined that the MU-UP signal is present in the received foot switch signal, the main body controller 56 modulates the main unit signal by the modulator 44b and controls the power supply circuit 60 such that the power supplied to the transmitter 46b is increased so that the transmit power is increased at step S41. Thereafter, the operational process proceeds to step S42.

At step S42, the modulated and amplified main unit signal is transmitted to the foot switch 14 from the antenna 19b by way of the branching filter 48b.

If the receive power of the foot switch signal is detected, at step S38, to be equal to or higher than the reference level OL, confirmation is made, at step S43, as to whether or not the pedal open/close signal indicates the pedal-open state. If the pedal open/close signal is determined to indicate the pedal-closed state, the operational process then proceeds to step S44 to allow the handpiece 22 to output ultrasonic vibration to perform treatment.

At the next step S45, the main body controller 56 produces the FSW-DOWN signal at first, and then produces the main unit signal by adding this FSW-DOWN signal to the identification ID contained in the foot switch signal. Thereafter, the operational process proceeds to step S48.

Contrarily, if the pedal open/close signal is determined, at step S43, not to indicate the pedal-closed state, outputting of ultrasonic vibration is stopped at step S46. Subsequently, the main body controller 56 produces, at step S47, the ultrasonic output stop signal at first, and then produces the main unit signal by adding this ultrasonic output stop signal to the identification D) contained in the foot switch signal.

At step S48, checking is performed as to whether or not the MU-UP signal is present in the received foot switch signal. If it is determined that the MU-UP signal is not present in the foot switch signal the operational process proceeds to step S50. Contrarily, if it is determined that the MU-UP signal is present in the foot switch signal, the power supply circuit 60 is controlled by the main body controller 56 such that the power supplied to the transmitter 46 is increased to thereby increase the transmit power of the main unit signal, and thereafter the operational process proceeds to step S50.

At step S50, the main unit signal which has been modulated nd amplified after the above processing is transmitted to the foot witch 14 from the antenna 19b by way of the branching filter 48b.

Referring back to the flow diagram of FIG. 5, if the received foot witch signal from the foot switch 14 which is in the connection elation with the apparatus main body 20 is determined, at step S32, as having been unrecognizable, or if the receive power of the received foot switch signal is determined, at step S38, to be lower than the reference level OL although the connection with the foot switch 14 is established, the main unit signal is produced by adding the FSW-UP signal to the identification ED of the possible foot switch 14.

Here, if the MU-UP signal is determined at step S40 to be present in the received foot switch signal, since it means that the receive power at the foot switch 14 side is insufficient, the power circuit 60 is controlled by the main body controller 56 at step S41 such that the power supplied to the transmitter 46b is increased to thereby increase the transmit power of the main unit signal, and then the main unit signal is transmitted to the foot switch 14 at step S42.

Here, attention is focused on the foot switch 14. The main unit signal which has been subjected to the above described processings as necessary is processed in accordance with the operational process shown in FIG. 7. Specifically, it is checked at step S10 whether or not the received main unit signal can be recognized correctly. If it is not recognizable, the controller 42 produces the MU-UP signal at step S11, and thereafter the operational process moves to step S4 shown in FIG. 4.

Contrarily, if the main unit signal is determined as having been correctly recognized at step S10, identification IDs are separated from the main unit signal, and it is checked whether or not the identification ID of the foot switch 14 is included in the separated identification IDs at step S12. If the check result is negative, it is determined that the received main unit signal is not the one from the expected main body apparatus 20, and the operational process terminates temporarily at step S13 and returns to step S31 to wait for another main unit signal. If the check result is affirmative, the controller 42 determines that the mutual authentication with the expected apparatus main body 20 has been done, and thereafter the operational process moves to step S14.

At step S14, the transmit power of the foot switch signal is checked as to whether or not it is lower than the value UV. If the transmit power is determined as reaching the value UV, the transmit power of the foot switch signal is inhibited from becoming more higher in view of the effects which the radio wave gives to the environment. Specifically the controller 42 produces at step S15 a malfunction occurrence signal after detecting that the transmit power is determined as reaching the value UV at step S14. At the subsequent step S16, the operator is informed of the fact that the communication between the foot switch 14 and the apparatus main body 20 cannot be established for some reason by an appropriate alarm generating means such as a buzzer.

Contrarily, if the transmit power is determined, at step S14, to be lower than the value UV it means that transmit power can be increased. In this case the operational process proceeds to step S17. At step S17, the controller 42 controls the power supply management part 54 according to the FSW-UP signal contained in the main unit signal such that the power supplied to the transmitter 46a from the storage battery 55 is increased. Thus, the transmit power of the foot switch signal transmitted from the transmitter 46a is increased. After that, the operational process returns to step S4 shown in FIG. 4.

Likewise, in a case where it is determined that the receive power at the foot switch 14 side is equal to or higher than the reference level OL at step S38 shown in FIG. 5, and that the pedal open/close signal contained in the foot switch signal indicates the "closed state" at step S43, the ultrasonic output is generated by the handpiece 22 at step S44, and the main unit signal is generated by adding the FSW-DOWN signal to the identification ID of the foot switch as a communication target.

On the other hand, in a case where the pedal open/close signal indicates the "open" state, that is, in a case where the operator intends to stop the ultrasonic output, the ultrasonic output by the handpiece 22 is stopped at step S46, and the main unit signal is produced by adding the ultrasonic output stop signal to the identification ID of the foot switch 14 at step S47, even when the receive power is determined to be higher than the reference level OL.

Further, in a case where it is determined that the MU-UP signal is present in the received foot switch signal at step S48, since it means that the receive power at the foot switch 14 side is insufficient, the power supply circuit 60 is controlled by the main body controller 56 at step S41 such that the power supplied to the transmitter 46b is increased to thereby increase the transmit power of the main unit signal. After that the main unit signal is transmitted to the foot switch 14 at step S42.

Here, attention is again focused on the foot switch 14. The main unit signal which has been subjected to the above described processings as necessary is processed in accordance with the operational process shown in FIG. 8. Specifically, it is checked at step S18 whether or not the received main unit signal can be recognized correctly by the controller 42. If it is difficult to recognize the main unit signal correctly, the controller 42 produces the MU-UP signal at step S19 to increase the transmit power of the main unit signal. Thereafter, the operational process moves to step S4 in FIG. 4, as a result of which the foot switch signal is produced.

Contrarily, if the main unit signal is determined, at step S18, as having been correctly recognized, identification IDs are separated from the main unit signal, and it is checked whether or not the identification ID of the foot switch 14 is included in the separated identification IDs at step S20. If the check result is negative, it is determined that the received main unit signal is not the one from the expected main body apparatus 20, and the operational process terminates temporarily at step S21 and returns to step S31 to wait for another main unit signal. If the check result is affirmative, the controller 42 determines that the mutual authentication with the expected apparatus main body 20 has been done, and thereafter the operational process moves to step S22.

At step S22, it is confirmed whether or not the FSW-DOWN signal is present in the received main unit signal. If the main unit signals is determined as not containing the FSW-DOWN signal the operational process returns to step S5 shown in FIG. 4 to wait for another main unit signal.

On the other hand, if the received main unit signal is determined, at step S22, as containing the FSW-DOWN signal, it is confirmed whether or not the transmit power of the foot switch signal is higher than the specified lower limit value at step S23. Only if the transmit power is determined to be higher than the lower limit value, the controller 42 reduces the power supplied to the supply management part 54 by one step at step S24.

Incidentally, when the transmit power of the foot switch signal is lower than the specified lower limit value, the power supplied to the supply management part 54 is not changed, because it is necessary for the transmit power of the foot switch signal to have a sufficient margin to thereby have resistance to external noise. In either case, the operational process returns to step S5 in FIG. 4 to wait for another main unit signal.

As described above, in the ultrasonic surgical system 12 of the present embodiment, the main body controller 56 of the apparatus main body 20 detects the receive power of the foot switch signal transmitted from the foot switch 14, and returns a signal commanding increase or reduction of the transmit power of the foot switch signal to the foot switch 14 depending on the detection result. Upon receipt of this signal, the controller 42 of the foot switch 14 increases or reduces the transmit power of the foot switch signal by controlling power to be supplied to the transmitter 46a through the power supply management part 54. Thus, according to the present embodiment, because the transmit power of the foot switch signal is automatically controlled to a suitable value, power consumption of the foot switch 14 can be reduced, while ensuring radio communication between the foot switch 14 and the apparatus main body 20.

Specifically, when the receive power of the foot switch signal is lower than the reference level OL, the main body controller 56 returns the FSW-UP signal to the foot switch 14 to increase the transmit power of the foot switch signal. In this way, the present embodiment is configured such that the transmit power is increase only when the receive power of the foot switch signal is low. Thus, according to the present embodiment, useless consumption of power stored in the storage battery 55 of the foot switch 14, which would otherwise be caused by unnecessary increase of the transmit power, can be avoided.

Furthermore, when the transmit power of the foot switch signal exceeds the value UV, transmission of the foot switch signal is stopped, while generating a warning. Thus, if the radio communication is disturbed by abnormal conditions, it is possible to avoid the circumstance where the transmit power exceeds the regulation limit affecting the environment. In addition, this embodiment of the invention provides the radio-based foot switch capable of informing the people involved in the surgery including the operator of the occurrence of abnormality to thereby allow them to handle the abnormality safely.

When the receive power of the foot switch signal is higher than the reference level OL, the main body controller 56 returns the FSW-DOWN command signal to the foot switch 14 to reduce the transmit power of the foot switch signal. In this way, the present embodiment is configured such that, when the receive power of the foot switch signal becomes excessively large, the transmit power is reduced. Thus, according to the present embodiment, power consumption of the foot switch 14 can be reduced while assuring the radio communication reliability.

As explained above, the present embodiment has a configuration where the transmit power of the foot switch signal is controlled within a scope that the transmit power of the foot switch signal does not fall below the specified lower limit value. Accordingly, according to the present embodiment, reliability in communication between the foot switch 14 and the apparatus main body 20 can be improved by preventing interruption of communication due, for example, to noise.

With reference to FIGS. 9 to 15, the second embodiment of the present invention is described hereunder. The foot switch 14 and the apparatus main body 20 of the present embodiment have the same appearances and circuitries as those of the first embodiment. However, the present embodiment is different from the first embodiment in that an output command trigger and an output stop command trigger are used instead of the pedal open/close signal. The output trigger and the output stop trigger are pulse-like signals outputted at regular intervals. Accordingly, in this embodiment, the output command signal is formed by a train of regularly spaced pulses.

In the present embodiment, when the first pedal 16a or the second pedal 16b has changed from the open state to the closed state, the controller 42 of the foot switch 14 clears at least the output stop command trigger and produces the output command trigger at regular intervals while the first pedal 16a or second pedal 16b is in the closed state. Contrarily, when the first pedal 16a or the second pedal 16b has changed from the closed state to the open state, the controller 42 clears at least the output command trigger and produces the output stop trigger by the number of times settable at any value. These output command and output stop command triggers are included in the foot switch signal.

The apparatus main body 20 of the present embodiment outputs ultrasonic vibration while receiving the output command trigger and receiving no output stop command trigger, and otherwise stops the output of ultrasonic vibration. The apparatus main body 20 of the present embodiment also returns the ultrasonic output stop signal to the foot switch 14 upon receiving the output stop command trigger. This ultrasonic output stop signal is included in the main unit signal.

In the present embodiment, if a state of receiving neither the output command trigger nor the output stop command trigger continues for a time after receiving any output command trigger, the apparatus main body 20 counts the duration of this state (hereinafter referred as signal loss time). If the signal loss time exceeds a specified period (allowable time in the order of several hundred ms at longest), the apparatus main body 20 determines malfunction as having occurred, and stops outputting ultrasonic vibration and returns an ultrasonic output stop signal to the foot switch 14. However, if the signal loss time is within the specified period, the apparatus main body 20 determines that the communication condition has only temporarily deteriorated, and continues outputting ultrasonic vibration.

In the present embodiment, the number of lost pulses, i.e. the number of output command triggers or output stop command triggers that should have been received but not actually have been received, are counted by a counter (not shown). Then, a determination is made as to whether or not the signal loss time has exceeded the specified period by comparing the counted value of the counter with a preset threshold value.

In the present embodiment, the transmit power of the foot switch signal is controlled to such a level that the receive power of the output command triggers is maintained between an upper limit level (referred to as the level OUL (Optional Upper limit Level)) and a lower limit level (refereed to as the level OLL (Optional Lower limit Level) both of which can be set at any values. Particularly, if the receive power of the output command triggers is higher than the level OUL, the main body controller 56 returns the FSW-DOWN signal to the foot switch 14, and if it is lower than the level OLL, returns the FSW-UP signal to the foot switch 14. While the receive power of the output command triggers is at an appropriate level between the level OUL and the level OLL, any command for changing the transmit power is transmitted to foot switch 14.

Next, an example of the transmit power adjusting procedure is explained with reference to FIG. 9.

Figure 9:
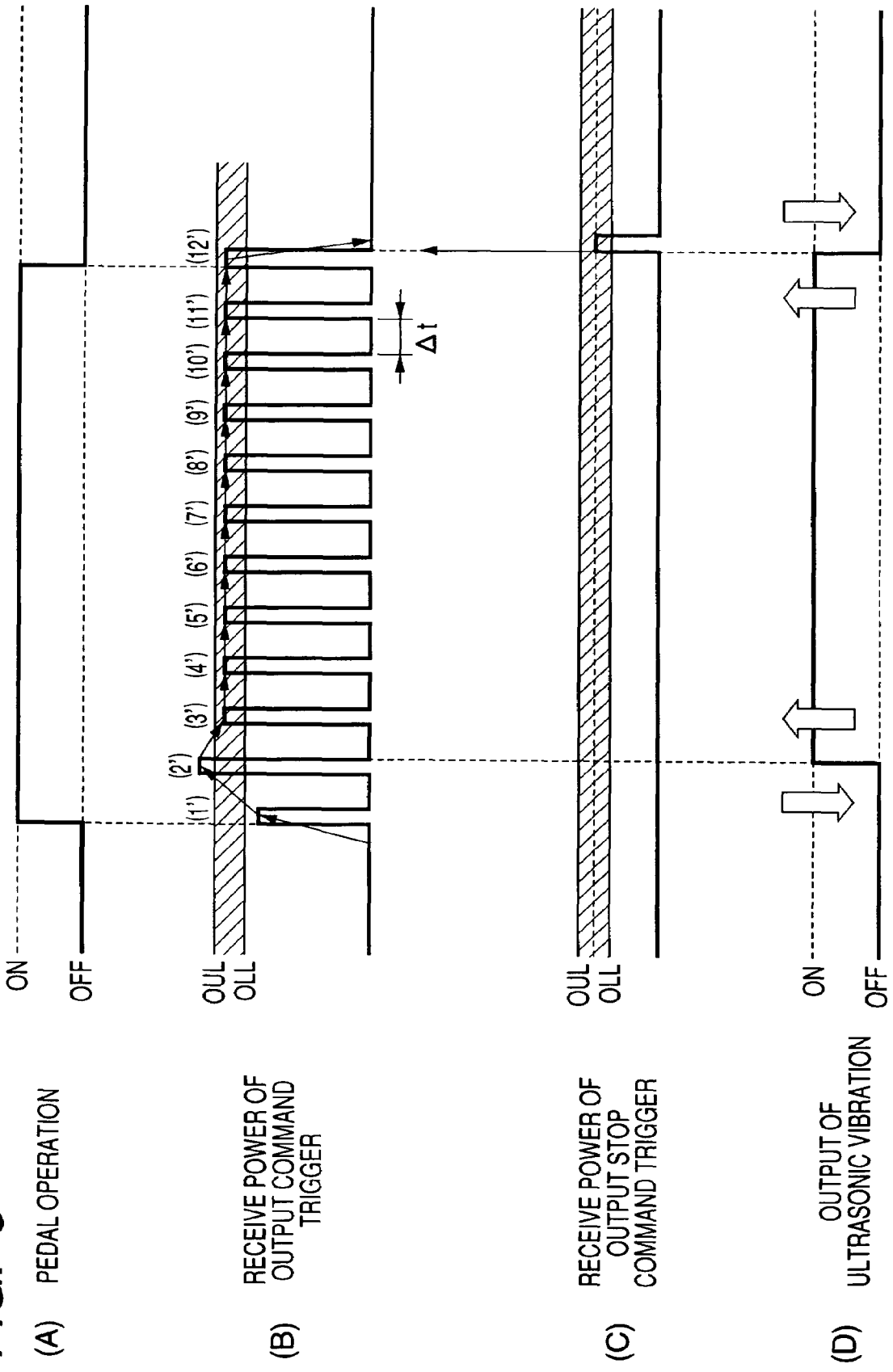
FIG. 9 is a diagram showing temporal variations of the transmission intensities of output command triggers and output stop command triggers which are transmitted as the foot switch signal from the foot switch when foot switch pedals are operated, and showing temporal variation of ON/OFF status of the ultrasonic vibration output in the apparatus main body, in an ultrasonic surgical system of a second embodiment according to the present invention.

When the first pedal 16*a* or the second pedal 16*b* of the foot switch 14 is operated or depressed (see (A) in FIG. 9), the output command triggers are transmitted at a regular interval Δt as a part of the foot switch signal, and received by the apparatus main body 20. As shown by (B) in FIG. 9, if the receive power is at level (1') lower than the level OLL, the FSW-UP signal is returned from the apparatus main body 20 to the foot switch 14 as a part of the main unit signal. As a result, the transmit power of the next transmitted foot switch signal is increased, and thereby the receive power is increased to level (2').

If the level (2') is higher than the level OLL, the apparatus main body 20 outputs ultrasonic vibration (see (D) in FIG. 9). In this example, as shown by (B) in FIG. 9, since the level (2') is higher than the level OUL, the FSW-DOWN signal is returned from the apparatus main body 20 to the foot switch 14 as a part of the main unit signal. As a result, the transmit power of the next transmitted foot switch signal is reduced, and thereby the receive power is reduced to level (3').

During the time when the receive power is at an appropriate level between the lower limit level and the upper limit level (levels (3') to (12') shown by (B) in FIG. 9), the USW-UP signal or FSW-DOWN signal is not transmitted to the foot switch 14, and the transmit power is maintained at substantially the same level. As a result, the apparatus main body 20 keeps outputting ultrasonic vibration while receiving the output command triggers.

When the depression of the foot switch 14 is released, the output stop command trigger is transmitted from the foot switch 14 to the apparatus main body 20 as a part of the foot switch signal. Upon receipt of the output stop command-trigger (see (C) in FIG. 9), the apparatus main body 20 stops outputting ultrasonic vibration (see (D) in FIG. 9).

Figure 10:
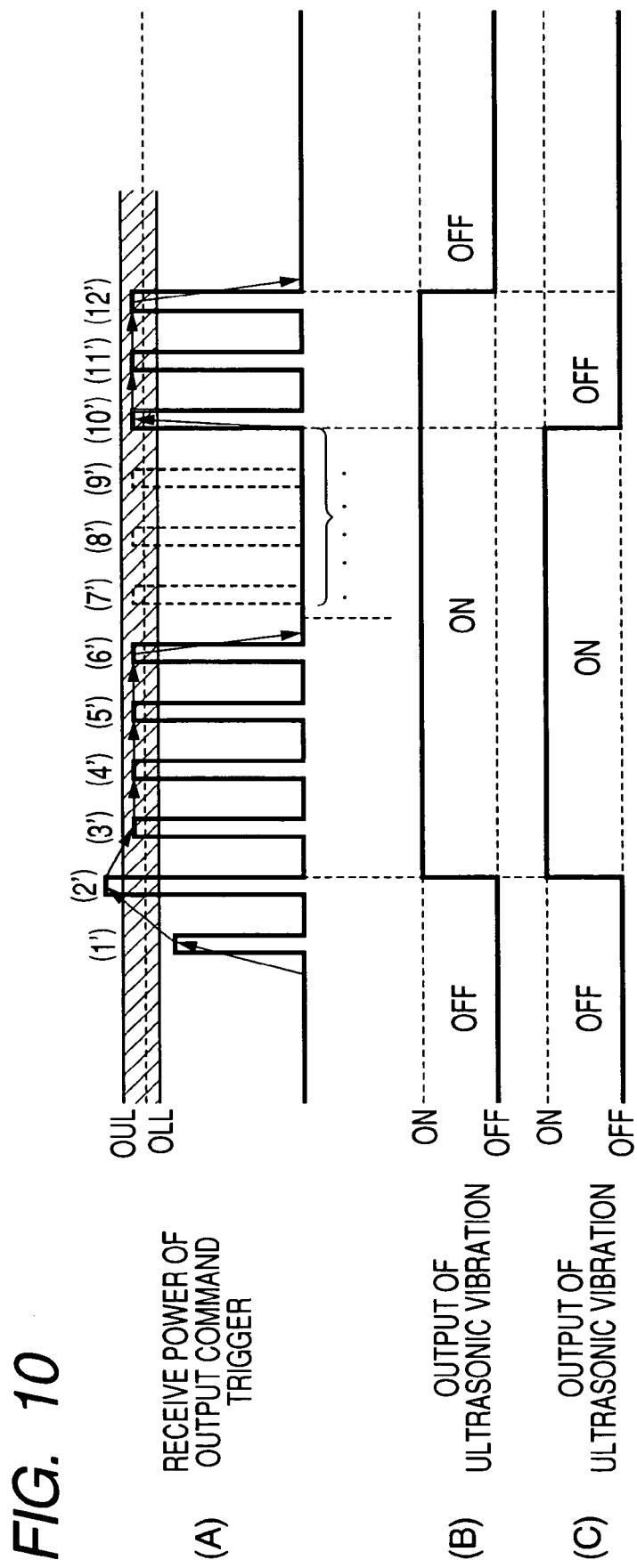
FIG. 10 is a diagram showing temporal variation of ON/OFF status of the ultrasonic vibration output in the apparatus main body when some of the output command triggers transmitted from the foot switch are lost, in the ultrasonic surgical system of the second embodiment according to the present invention.

FIG. 10 shows a case where some of the pulses (output command triggers) are lost. Here assume that three output command triggers have been lost during a period of 3Δt.

In this case, since the number of the lost pulses is 3, if a threshold value is set at 4 or more, the output of the ultrasonic vibration is kept as shown by (B) in FIG. 10. On the other hand, if a threshold value is set at 3 or below, the output of the ultrasonic vibration is stopped as shown by (C) in FIG. 10.

Hereinafter is described the operational process of the ultrasonic surgical system of the present embodiment, with reference to the flow diagrams of FIGS. 11 to 15.

Figure 11:
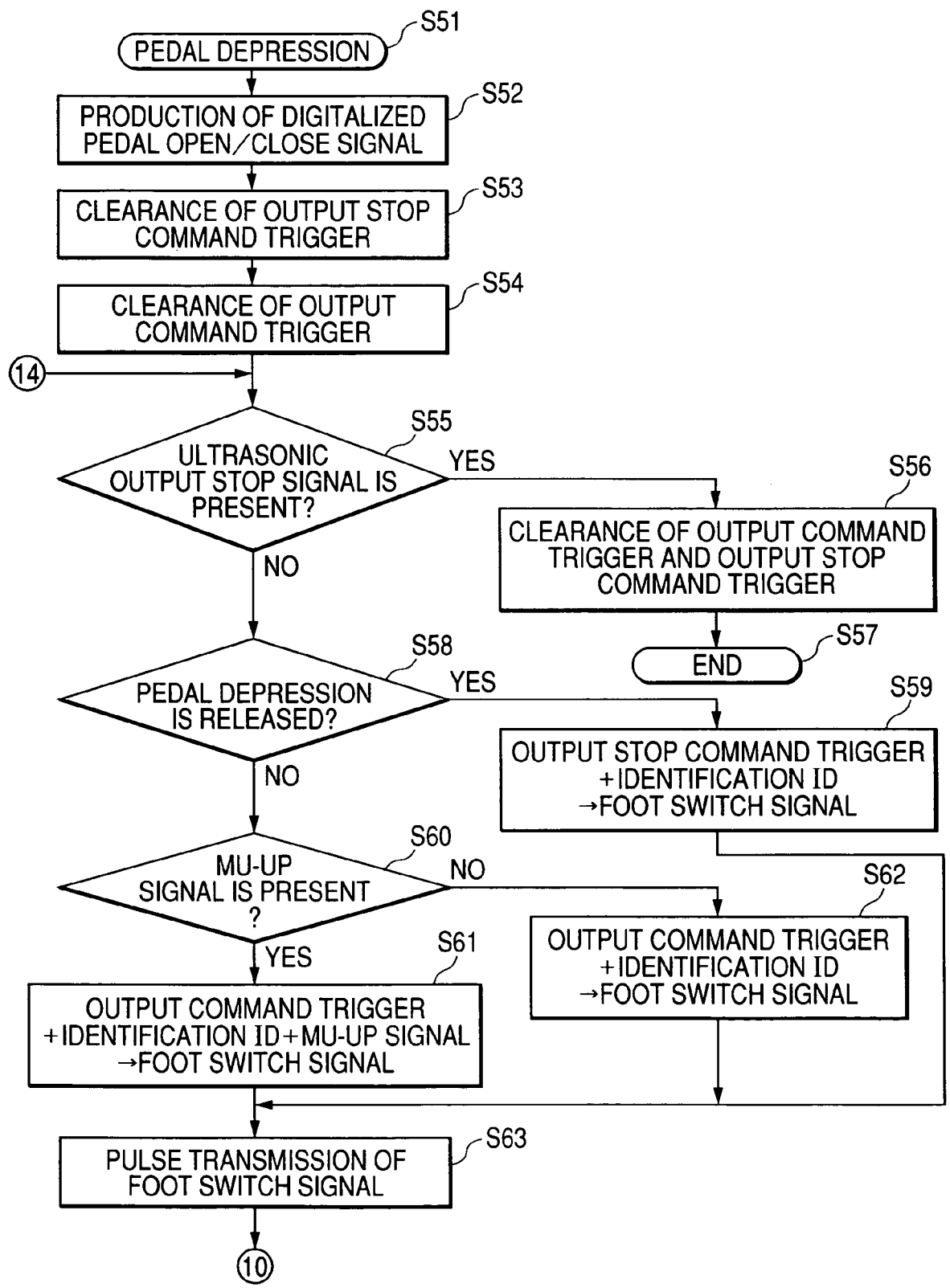
FIGS. 11 to 15 are flow diagrams illustrating the operations of the ultrasonic surgical system of the second embodiment according to the present invention.

When the first pedal 16*a* or the second pedal 16*b* of the foot switch 14 is depressed at step S51 shown in FIG. 11, the controller 42 produces, at step S52, the digitalized pedal open/close signal indicative of an open state or a closed state of the pedal 16*a* or 16*b*. The controller 42 then clears, at step S53, the output stop command trigger, and produces, at step S54, the output command trigger.

As will be described later, when the output stop command trigger is transmitted from the foot switch 14 to the apparatus main body 20, or when the number of the lost pulses exceeds a specified value, the ultrasonic output stop signal is transmitted from the apparatus main body 20 to the foot switch 14, and reception of the ultrasonic output stop signal is checked at step S55. If it is determined, at step S55, that the ultrasonic output stop signal has been received, the output command trigger and the output stop command trigger are cleared, at step S56, to terminate the operational process (step S57). Contrarily, if it is determined, at step S55, that the ultrasonic output stop signal has not been received, the operational process proceeds to step S58.

At step S58, checking is performed as to whether or not depression of the first pedal 16*a* or the second pedal 16*b* has been released. If the depression is determined, at step S58, as having been released, the operational process moves to step S59. At step S59, the controller 42 forms the foot switch signal by producing the output stop command trigger, and by adding an identification ID to this output stop command trigger. Subsequently, the operational process proceeds to step S63. Contrarily, if the depression is determined, at step S58, as not having been released, the operational process proceeds to step S60.

At step S60, if the received main unit signal is difficult to correctly recognize, checking is performed as to whether or not the MU-UP signal commanding the apparatus main body 20 to increase the transmit power, has been produced. If it is determined, at step S60, that the MU-UP signal has been produced, the controller 42 produces, at step S61, the foot switch signal by adding the identification ID and the MU-UP signal to the output command trigger. After that, the operational process proceeds to step S63.

Contrarily, if it is determined, at step S60, that any MU-UP signal has not been produced, the controller 42 produces, at step S62, the foot switch signal by adding the identification ID to the output command trigger. After that, the operational process proceeds to step S63.

At step S63, the foot switch signal is transmitted from the foot switch 14 to the apparatus main body 20.

Figure 12:
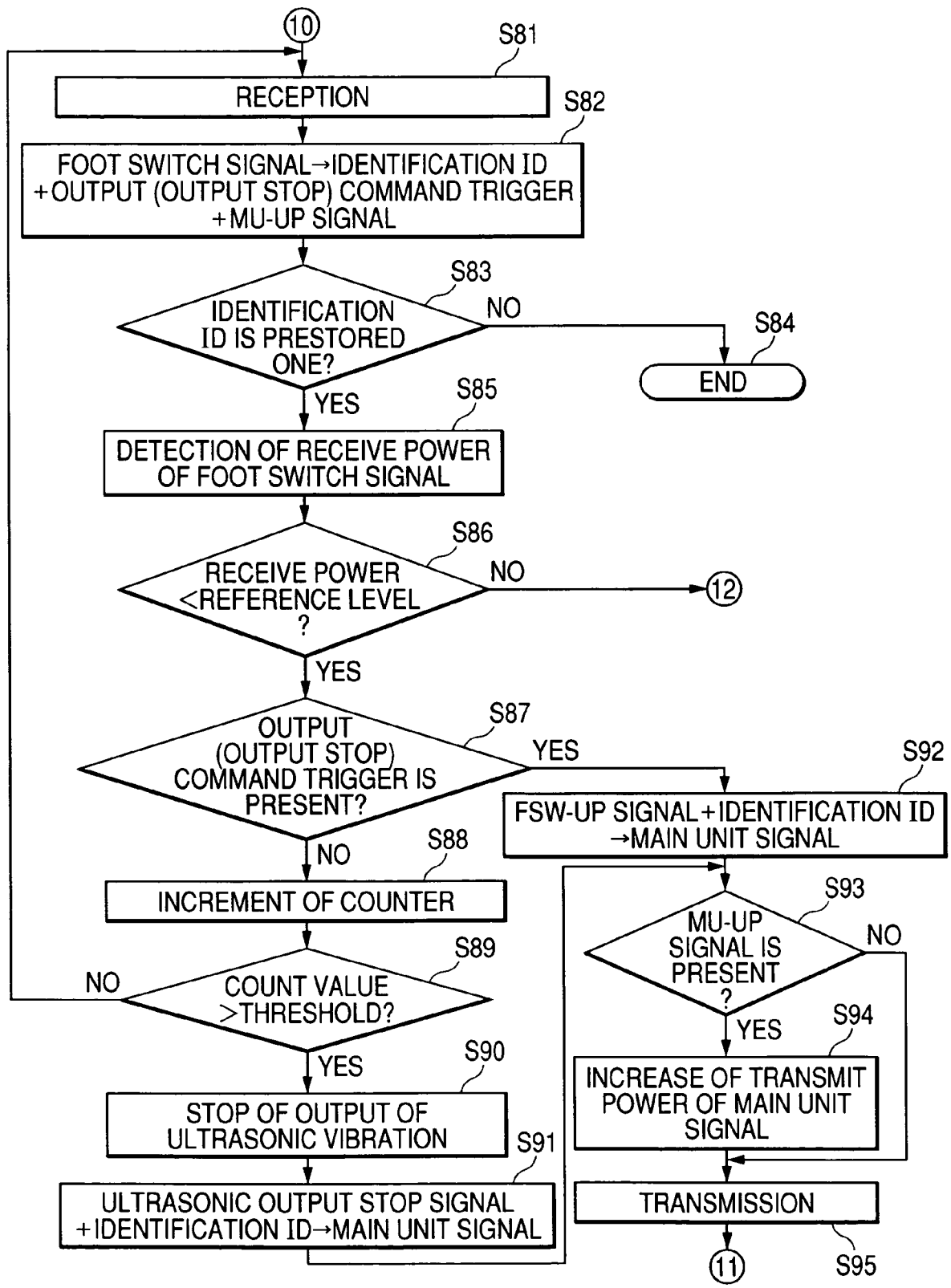

When the foot switch signals is received by the apparatus main body 20 at step S81 shown in FIG. 12, the main body controller 56 attempts to extract the identification ID, output command trigger (or output stop command trigger), and MU-UP signal from the foot switch signal. Subsequently, at step S83, the main body controller 56 makes a comparison of the extracted identification ID with the identification IDs pre-stored in the internal memory. If the extracted identification ID is determined as not being identical with any of the identification IDs prestored in the internal memory, the operational process is terminated (step S84). Contrarily, if the extracted identification ID is determined as being identical with one of the identification IDs prestored in the internal memory, the main body controller 56 detects, at step S85, receive power of the foot switch signal.

Subsequently, checking is performed, at step S86, as to whether or not the detected receive power is lower than the level OLL. If the receive power is determined to be lower than the level OLL, the operational process proceeds to step S87.

At step S87, the main body controller 56 checks whether or not any output command trigger or output stop command trigger has been received. If it is determined that neither of these triggers has been received, the count value of the counter counting the number of the lost pulses is incremented by one at step S88. Subsequently, the count value is checked at step S89, as to whether or not it is larger than a specified threshold value. If the count value is determined to be equal to or smaller than the specified value, the operational process returns to step S81. Thus, in a case where bad communication state continues, steps S81 to S89 are repeated, and thereby the count value of the counter is increased stepwise.

If the count value of the counter is determined, at step S89, to have exceeded the specified threshold value, the output of ultrasonic vibration is stopped. At the subsequent step S91, the main unit signal is formed by producing the ultrasonic output stop signal, and by adding the identification ID to this ultrasonic output stop signal. After that, the operational process proceeds to step S93.

On the other hand, if the output command trigger or output stop command trigger is determined, at step S87, as having been received, the main body controller 56 forms, at step S92, the main unit signal by adding the identification ID to the FSW-UP signal. After that, the operational process moves to step S93.

At step S93, checking is performed as to whether or not the MU-UP signal is present in the received foot switch signal. If it is determined that the MU-UP signal is not present in the foot switch signal, the operational process proceeds to step S95.

Contrarily, if it is determined, at step S93, that the MU-UP signal is present in the foot switch signal, the transmit power of the main unit signal is increased at step S94. After that, the operational process proceeds to step S95.

At step S95, the main unit signal formed at Step S91 containing the ultrasonic output stop signal and the identification ID, or the main unit signal formed at step S92 containing the FSW-UP signal and the identification ID, is transmitted from the apparatus main body 20 to the foot switch 14.

Figure 13:
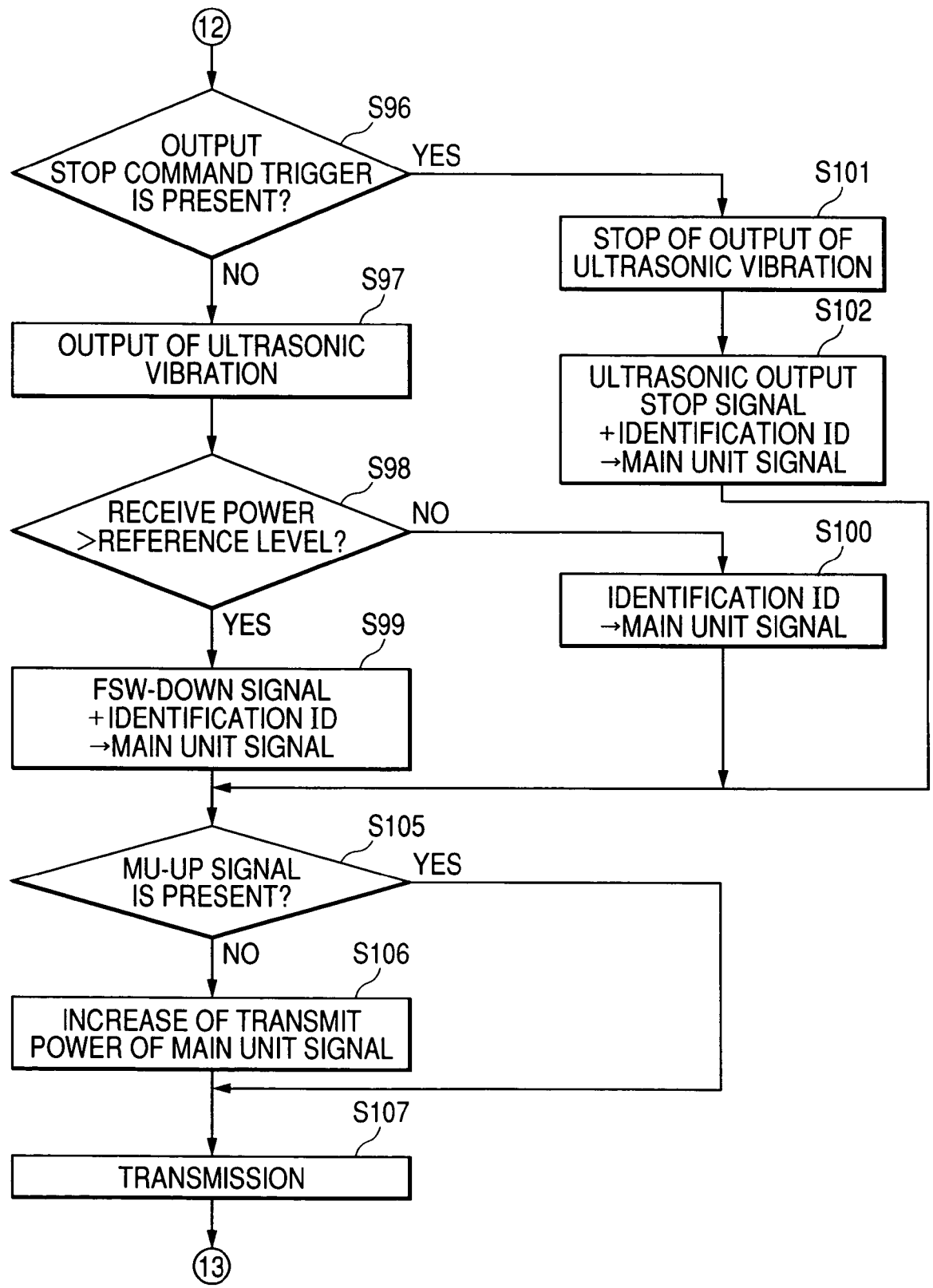

If the receive power of the foot switch signal is determined, at step S86, to be equal to or more than the level OLL, the operational process proceeds to step S96 shown in FIG. 13. At step S96, checking is performed as to whether or not the output stop command trigger is present in the received foot switch signal. If it is determined, at step S96, that no output stop command trigger is present in the foot switch signal, the apparatus main body 20 outputs ultrasonic vibration at step S97.

At the next step S98, the receive power of the foot switch signal is checked as to whether or not it is higher than the level OUL. If the receive power is determined, at step S98, to be higher than the level OUL, the main unit signal is formed, at the subsequent step S99, by adding the identification ID to the FSW-DOWN signal. After that, the operational process proceeds to step S105.

Contrarily, if the receive power is determined, at step S98, to be equal to or lower than the level OUL, the main unit signal containing the identification ID alone is formed at the subsequent step S100. After that, the operational process moves to step S105.

On the other hand, if the received foot switch signal is determined, at step S96, as containing the output stop command trigger, the apparatus main body 20 stops, at step S101, output of the ultrasonic vibration, and forms, at the next step S102, the main unit signal by adding the identification ID to the ultrasonic output stop trigger. After that, the operational process proceeds to step S105.

At step S105, checking is performed as to whether or not the MU-UP signal is present in the received foot switch signal. If it is determined that the MU-UP signal is present in the foot switch signal, the transmit power of the main unit signal is increased at step S106, and then the operational process proceeds to step S107. Contrarily, if it is determined that the MU-UP signal is not present in the foot switch signal, the operational process directly proceeds to step S107.

At step S107, the main unit signal formed at step S99 containing the FSW-DOWN signal and the identification ID, the main unit signal formed at step S100 containing the identification ID alone, or the main unit signal formed at step S101 containing the ultrasonic output stop signal and the identification ID, is transmitted from the apparatus main body 20 to the foot switch 14.

Figure 14:
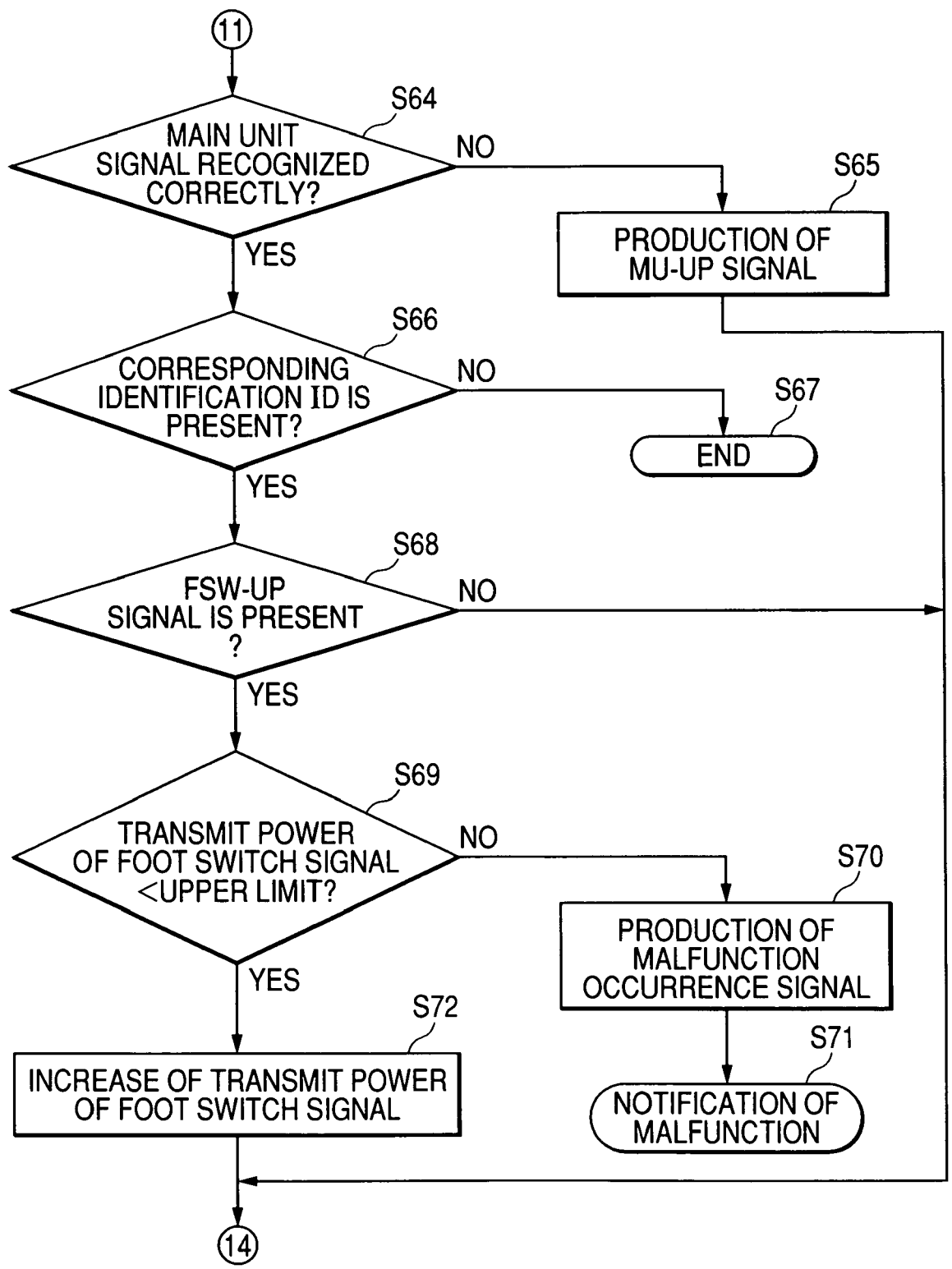
Figure 15:
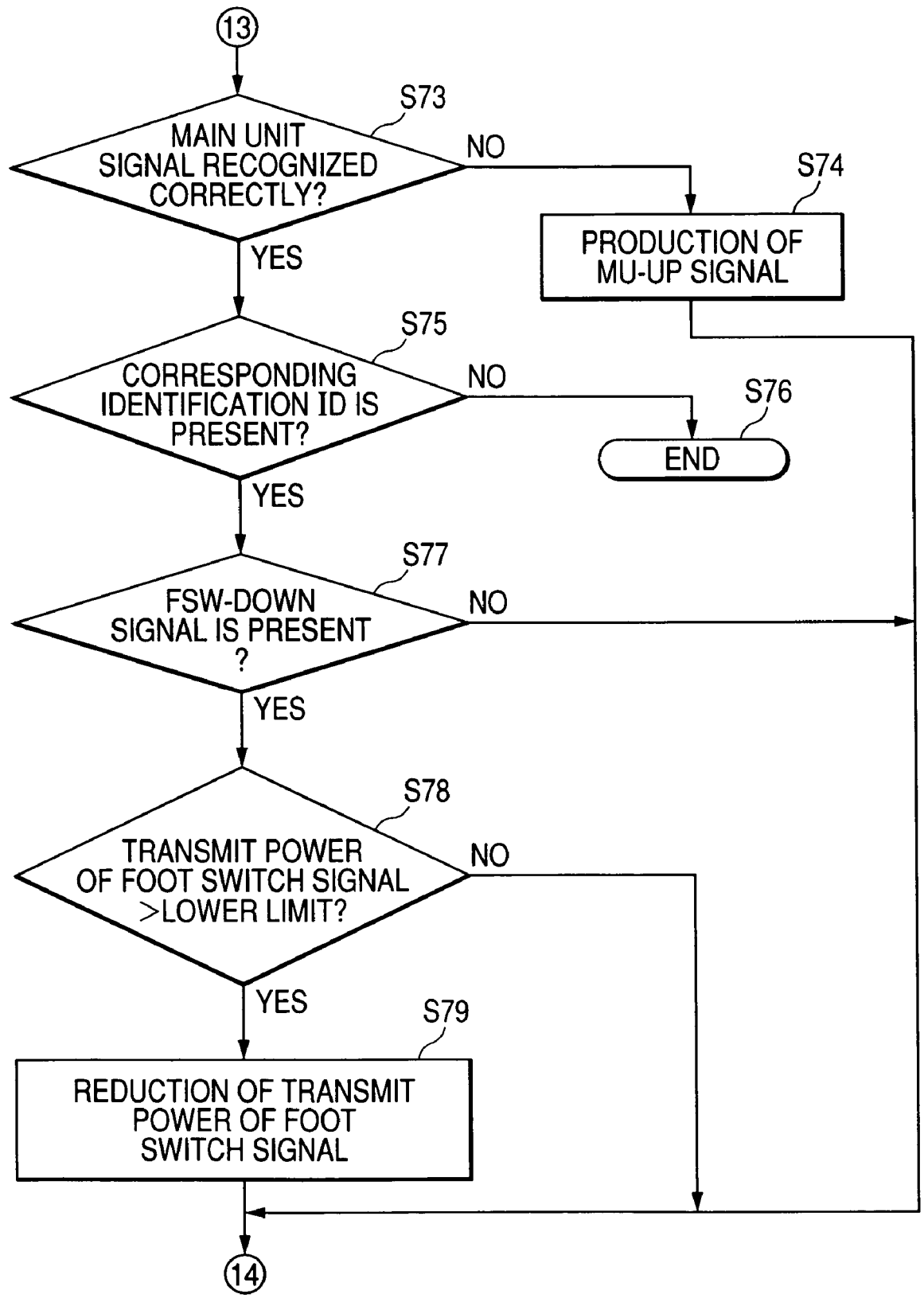

Referring back to the flow diagram in FIG. 12, when the main unit signal formed at step S91 containing the ultrasonic output stop signal and the identification ID, or the main unit signal formed at step S92 containing the FSW-UP signal and the identification ID, is transmitted from the apparatus main body 20 to the foot switch 14, the operational process proceeds to step S64 shown in FIG. 14.

Figure 7:
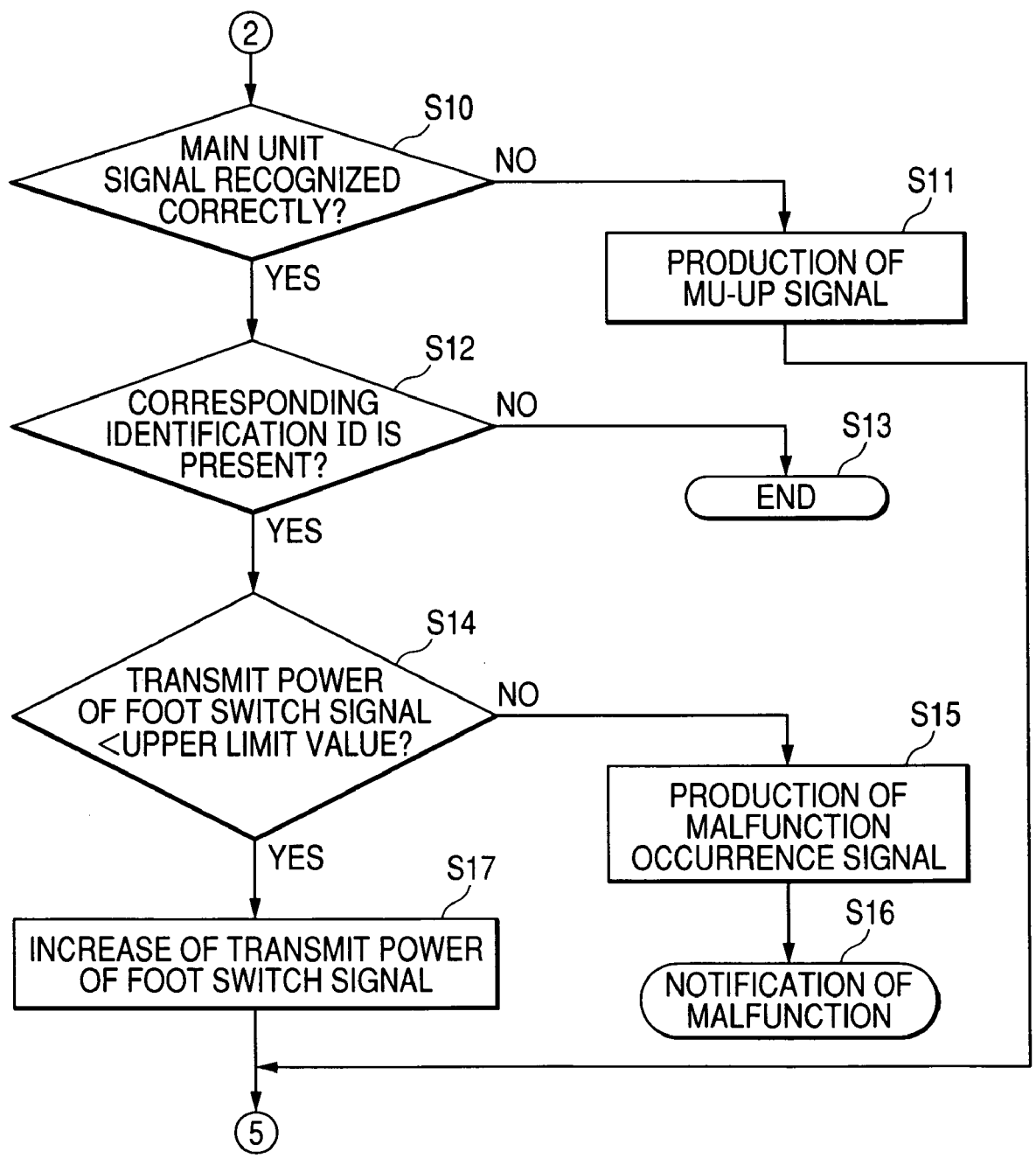
Figure 8:
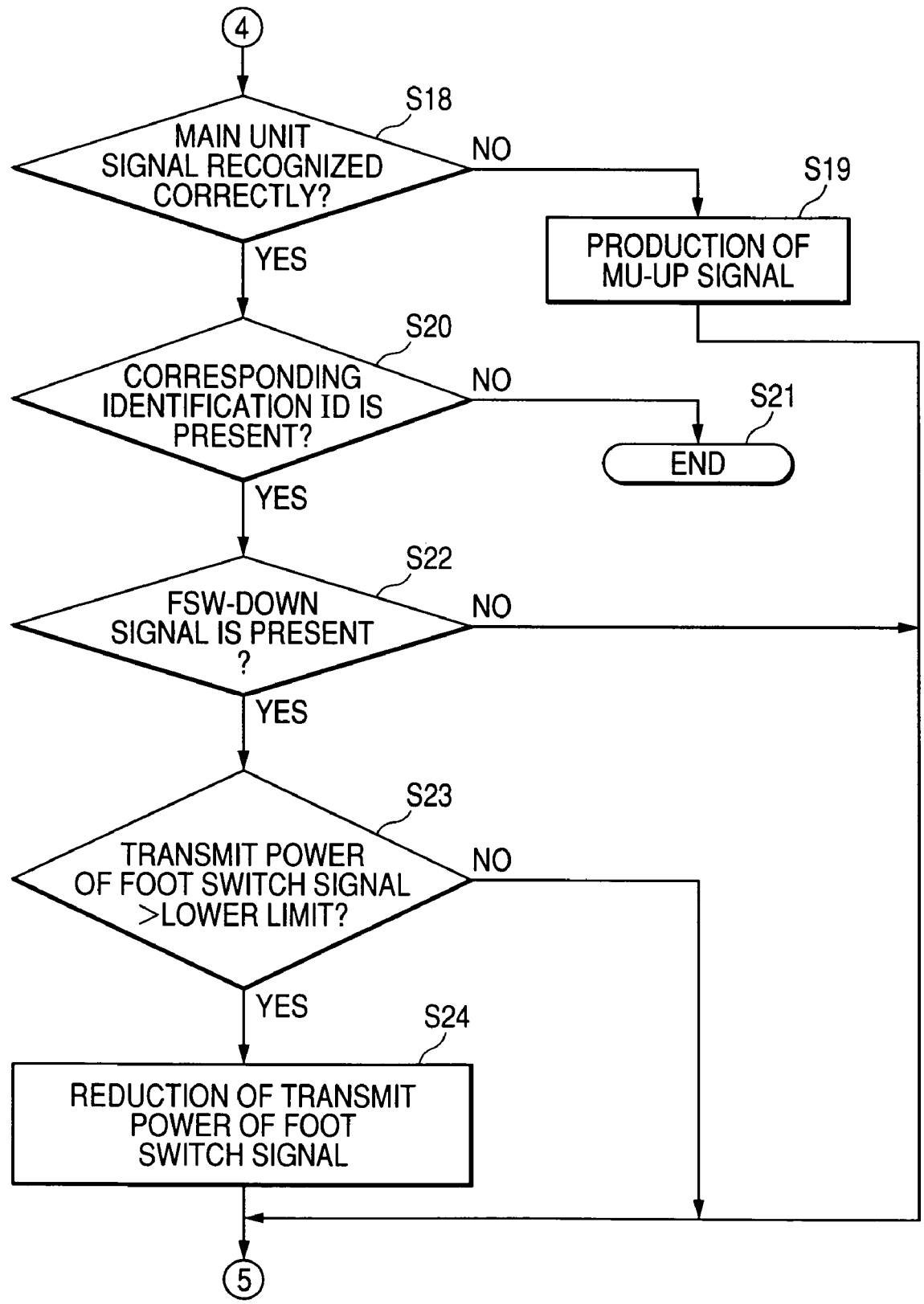

The processings at steps S64 to S72 shown in FIG. 14 are substantially the same as the processings at steps S10 to S17 shown in FIG. 7 associated with the first embodiment. Specifically, if it is determined, at step S64, that the main unit signal has not been correctly recognized, the operational process returns to step S14 to repeat the processings at steps S55 to S58.

Contrarily, if it is determined, at step S64, that the main unit signal has been correctly recognized, checking is performed, at the subsequent step S66, as to whether or not the identification ID unique to the foot switch 14 is present in the received main unit signal. If it is determined that the identification ID unique to the foot switch 14 is not present in the main unit signal, the operational process is terminated (step S67). If it is determined that the identification ID unique to the foot switch 14 is present, checking is performed, at the subsequent step S68, as to whether or not the FSW-UP signal is present in the main unit signal. If it is determined, at step S68, that the FSW-UP signal is present in the main unit signal (that is, if the ultrasonic output stop signal is present in the main unit signal), the operational process returns to step S55 shown in FIG. 11. Subsequently, after the processing at step S56 is performed, the operational process is terminated (step S57).

If it is determined, at step S68, that the FSW-UP signal is present in the received main unit signal, checking is performed, at step S69, as to whether or not the transmit power of the foot switch signal is lower than the upper limit level. If the transmit power of the foot switch signal is determined to be lower than the upper limit level, the transmit power of the foot switch signal is increased at step S72, 26 and then the operational process returns to step S55 shown in FIG. 11. Thereafter, processings at step S58 and the subsequent steps are repeated.

Contrarily, if the transmit power of the foot switch signal is determined, at step S69, to be equal to or higher than the upper limit level, a malfunction signal is produced at step S70, and the occurrence of malfunction is notified at step S71.

As described above, if the receive power of the foot switch signals is determined, at step S86 in FIG. 12, to be equal to or higher than the level OLL, processings at steps S15 to S107 shown in FIG. 13 are carried out, as a result of which the main unit signal containing the FSW-DOWN signal and the identification ID, or the main unit signal containing the identification ID alone, or the main unit signal containing the ultrasonic output stop signal and the identification ID, is transmitted from the apparatus main body 20 to the foot switch 14. Thereafter, the operational process proceeds to step S73 shown in FIG. 15.

The processings at steps S73 to S79 are the same as those at step S18 to S24 in the fist embodiment. Specifically, if the main unit signal is determined, at step S73, as not having been correctly recognized, the MU-UP signal is produced, at step S74, and then the operational process returns to step S55 shown in FIG. 11. Thereafter, the processings at step S58 and the subsequent steps are repeated.

On the other hand, if the received main unit signal is determined, at step S73, as having been correctly recognized, checking is performed, at the next step S75, as to whether or not the identification ID unique to the foot switch 14 is present in the main unit signal. If it is determined that the identification ID unique to the foot switch 14 is present in the main unit signal, the operational process is terminated (step S76).

If it is determined that the identification ID unique to the foot switch 14 is present in main unit signal, checking is performed, at the next step S77, as to whether or not the FSW-DOWN signal is present in the main unit signal. If it is determined that the FSW-DOWN signal is not present in the main unit signal, the operational process proceeds to step S55 shown in FIG. 11. Thereafter, if the received main unit signal includes the identification ID, processings at step S58 and the subsequent steps are repeated. If the received main unit signal includes the ultrasonic output stop signal and the identification ID, the output command trigger and output stop command trigger are cleared at step S56, and the operational process is terminated (step S57).

On the other hand, if it is determined, at step S77, that the FSW-DOWN signal is present in the main unit signal, checking is performed, at step S78, as to whether or not the transmit power of the foot switch signal is higher than the lower limit level. If the transmit power of the foot switch signal is determined to be higher than the lower limit level, the transmit power of the foot switch signal is reduced at step S79, and then the operational process returns to step S55. Contrarily, if the transmit power of the foot switch signal is determined to be equal to or lower than the lower limit level, the operational process directly returns to step S55. Thereafter, processings at step S55 and the subsequent steps are repeated.

In the ultrasonic surgical system 12 of the present embodiment, radio communication between the apparatus main body 20 and the foot switch 14 is carried out using pulse-like signals transmitted at regular intervals. Hence, the electrical power consumed in the foot switch 14 of the present embodiment is significantly reduced compared to the conventional systems in which signals are transmitted from a foot switch to an apparatus main body in a consecutive manner.

Moreover, the ultrasonic surgical system 12 of the present embodiment is configured such that, when the output command triggers transmitted from the foot switch 14 are lost, the apparatus main body 20 continues outputting ultrasonic vibration as long as the signal loss time is within a specified time period. This configuration enables avoiding interruption of the output of the ultrasonic vibration due to a short-period communication deterioration, and thereby improving the reliability of the system.

Although the present invention has been described by way of several ultrasonic surgical systems, the present invention is applicable to any system employing a wireless foot switch. For example, the present embodiment is applicable to a system which includes an imaging device such as a flexible endoscope or a rigid endoscope, and performs freezing, recording, GAIN control, magnification control, rotation or the like on picture images by use of the foot switch.

What is claimed is:

1. A surgical system including a foot switch and an apparatus main body having a function of producing active surgical output, the foot switch comprising:
a pedal;
an output command signal generating section generating an output command signal when the pedal is operated;
a foot switch communication section performing communication directly with the apparatus main body;
a monitoring section monitoring a state of the output command signal generating section;
a transmit power adjusting section adjusting transmit power of the output command signal in the foot switch communication section;
a warning signal indicating section indicating a warning signal;
a control section controlling the output command signal generating section and the warning signal indicating section based on a monitoring result of the monitoring section; and
a storage battery supplying electric power to the output command signal generating section, the foot switch communication section, the transmit power adjusting section, the warning signal indicating section, the monitoring section, and the control section;

the apparatus main body comprising:
a main body communication section performing communication directly with the foot switch;
an output producing section producing active surgical output in accordance with the output command signal transmitted to the main body communication section from the foot switch and received by the main body communication section; and
a receiving-condition detecting section detecting, as a receiving condition, receive power of the output command signal in the main body communication section and generating a signal indicative of the detected receiving condition, wherein the transmit power adjusting section adjusts by temporal variation the transmit power stepwise with a predetermined increment and at predetermined time intervals on the basis of a comparison result between a predetermined level settable at any value, and the signal indicative of the receive power, the signal being detected by the receiving-condition detection section, transmitted from the main body communication section and received by the foot switch communication section in order to reduce electric power supplied by the storage battery and to keep the receive power around a constant level, the output command signal generating section is configured to stop generating the output command signal when the transmit power exceeds a specified upper limit value, the warning indicating section is configured to generate the warning signal when the transmit power exceeds the specified upper limit value, the transmit power adjusting section is configured to adjust the transmit power such that the transmit power does not fall below a specified lower limit value even if the signal indicative of the receive power is at a level exceeding the settable predetermined level, and the receiving-condition detecting section is configured to command the transmit power adjusting section to increase or reduce the transmit power when receive power of the output command signal in the main body communication section is out of a range between predetermined levels settable to arbitrary value.

2. The surgical system according to claim 1, wherein the active output producing section includes an ultrasonic vibrating element.

3. The surgical system according to claim 1, wherein the output command signal generating section generates a train of regularly spaced pulses as the output command signal while the pedal is operated, the train of pulses including at least one output command trigger pulse commanding the apparatus main body to produce active surgical output and an output stop command trigger pulse commanding the apparatus main body to stop producing active surgical output.

4. The surgical output system according to claim 3, wherein the output producing section includes an ultrasonic vibrating element.

5. The surgical system according to claim 3, wherein the apparatus main body further comprises a control section which commands the output producing section to stop producing the active surgical output if the control section detects that reception of the output command signal from the foot switch is interrupted over a period of time longer than a predetermined time, and otherwise commands the output producing section to continue producing the active surgical output, and further comprises a warning signal indication section which indicates a warning signal if the control section detects that reception of the output command signal from the foot switch is interrupted over a period of time longer than the predetermined time.

6. The surgical system according to claim 3, wherein the apparatus main body further comprises a control section and the surgical system further comprises other foot switches each of which having assigned an identification number registered in the control section, wherein the control section operates to extract identification ID from the output command signal transmitted from the foot switch, and if the control section fails to detect identification ID assigned to the foot switch, transmits a communication signal to all other foot switches assigned identification IDs registered in the control section through the main body communication section.

7. The surgical system according to claim 6, wherein the communication signal includes a command signal commanding to increase transmit power of the foot switch.

8. The surgical system according to claim 1, wherein the control section commands the output producing section to stop producing the active surgical output if the control section detects that reception of the output command signal from the foot switch is interrupted over a period of time longer than a predetermined time, and otherwise commands the output producing section to continue producing the active surgical output, and the warning signal indication section indicates the warning signal if the control section detects that reception of the output command signal from the foot switch is interrupted over a period of time longer than the predetermined time.

9. The surgical system according to claim 1, further comprising other foot switches each of which having assigned an identification number registered in the control section wherein the control section operates to extract identification ID from the output command signal transmitted from the foot switch, and if the control section fails to detect identification ID assigned to the foot switch, transmits a communication signal to all other foot switches assigned identification IDs registered in the control section through the main body communication section.

10. The surgical system according to claim 9, wherein the communication signal includes a command signal commanding increasing transmit power of the foot switch.

11. A foot switch for a surgical system comprising:

a pedal;

an output command signal generating section generating, when the pedal is operated, an output command signal commanding an apparatus main body having a function of producing active surgical output to produce active surgical output;

a communication section performing communication with the apparatus main body;

a monitoring section monitoring a state of the output command signal generating section;

a transmit power adjusting section adjusting transmit power of the output command signal in the communication section;

a warning signal indicating section indicating a warning signal;

a control section controlling the output command signal generating section and the warning signal indicating section based on a monitoring result of the monitoring section; and a storage battery supplying electric power to the output command signal generating section, the communication section and the transmit power adjusting section, the warning signal indicating section, the monitoring section, and the control section, wherein the transmit power adjusting section is adapted to adjust by temporal variation the transmit power stepwise with a predetermined increment and at predetermined time intervals on the basis of a comparison result between a predetermined level settable at any value, and a signal indicative of receive power of the output command signal in the apparatus main body, the signal transmitted from the apparatus main body and received by the communication section in order to reduce electric power supplied by the storage battery and to keep the receive power around a constant level, the output command signal generating section is configured to stop generating the output command signal when the transmit power exceeds a specified upper limit value, the warning indicating section is configured to generate the warning signal when the transmit power exceeds the specified upper limit value, and the transmit power adjusting section is configured to adjust the transmit power such that the transmit power does not fall below a specified lower limit value even if the signal indicative of the receive power is at a level exceeding the settable predetermined level.

12. The foot switch according to claim 11, wherein the output command signal generating section generates a train of regularly spaced pulses as the output command signal while the pedal is operated, the train of pulses including at least one output command trigger pulse commanding the apparatus main body to produce active surgical output and an output stop command trigger pulse commanding the apparatus main body to stop producing active surgical output.

* * * * *